United States Patent
Lobdill et al.

(10) Patent No.: US 10,627,357 B2
(45) Date of Patent: *Apr. 21, 2020

(54) DIGITAL PATCH-CLAMP AMPLIFIER

(71) Applicant: Sutter Instrument Company, Novato, CA (US)

(72) Inventors: Rich Lobdill, San Anselmo, CA (US); Aaron Best, Novato, CA (US); Greg Hjelmstad, Ross, CA (US)

(73) Assignee: Sutter Instrument Company, Novato, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/184,923

(22) Filed: Nov. 8, 2018

(65) Prior Publication Data

US 2019/0072509 A1 Mar. 7, 2019

Related U.S. Application Data

(63) Continuation-in-part of application No. 14/859,227, filed on Sep. 18, 2015, now Pat. No. 10,393,727.

(51) Int. Cl.
*G01N 33/487* (2006.01)
*G01N 27/02* (2006.01)
*G01N 27/04* (2006.01)

(52) U.S. Cl.
CPC ......... *G01N 27/045* (2013.01); *G01N 27/041* (2013.01); *G01N 33/48728* (2013.01)

(58) Field of Classification Search
CPC ....... G01N 33/48728; G01N 33/48785; G01R 27/028

See application file for complete search history.

(56) References Cited

U.S. PATENT DOCUMENTS

| 4,441,507 A | 4/1984 | Steffin |
| 4,510,442 A | 4/1985 | Neher |

(Continued)

FOREIGN PATENT DOCUMENTS

| CN | 103713270 | 4/2014 |
| CN | 105519133 | 4/2016 |

(Continued)

OTHER PUBLICATIONS

CN201680062644.0, "Office Action", dated Jul. 3, 2019, 10 pages.

(Continued)

*Primary Examiner* — Walter L Lindsay, Jr.
*Assistant Examiner* — Milton Gonzalez
(74) *Attorney, Agent, or Firm* — Kilpatrick Townsend & Stockton, LLP

(57) ABSTRACT

Patch-clamp amplifiers that may be readily manufactured, may be simple to reconfigure for product updates, and can be quickly reconfigured into a different mode during operation. One example may provide patch-clamp amplifiers that may be readily manufactured by implementing some or all of the compensation and other circuits using digital circuitry. These digital circuits may be implemented using discrete or integrated logic circuits, programmable logic such as field-programmable gate arrays or programmable logic arrays, or other fixed or configurable logic circuits or combination thereof. These programmable logic circuits may be reconfigured by a user or by a manufacturer through firmware or software updates when a product update is desired. These circuits may also be quickly reconfigured to allow rapid switching between modes during use.

18 Claims, 31 Drawing Sheets

(56) References Cited

U.S. PATENT DOCUMENTS

| | | | |
|---|---|---|---|
| 6,163,719 | A | 12/2000 | Sherman et al. |
| 6,700,427 | B1 | 3/2004 | Sherman et al. |
| 6,932,893 | B2 | 8/2005 | Bech et al. |
| 7,489,965 | B2 | 2/2009 | Sun et al. |
| 7,741,829 | B2 | 6/2010 | Tanaka et al. |
| 7,940,105 | B2 | 5/2011 | Quesada et al. |
| 8,000,783 | B2 | 8/2011 | Sun et al. |
| 8,163,527 | B2 | 4/2012 | Tanaka |
| 9,071,209 | B1 | 6/2015 | Harrison |
| 2004/0234943 | A1 | 11/2004 | Lepple-wienhues |
| 2007/0057720 | A1 | 3/2007 | Hand et al. |
| 2013/0341192 | A1 | 12/2013 | Dunbar et al. |
| 2017/0082600 | A1 | 3/2017 | Lobdill |

FOREIGN PATENT DOCUMENTS

| | | |
|---|---|---|
| WO | 2017048635 | 3/2017 |
| WO | 2017048635 | 5/2017 |

OTHER PUBLICATIONS

U.S. Appl. No. 14/859,227, "Final Office Action", dated Dec. 14, 2018, 11 pages.

U.S. Appl. No. 14/859,227, "First Action Interview Office Action Summary", dated May 25, 2018, 5 pages.

U.S. Appl. No. 14/859,227, "First Action Interview Pilot Program Pre-Interview Communication", dated Feb. 22, 2018, 4 pages.

U.S. Appl. No. 14/859,227, "Restriction Requirement", dated Jul. 17, 2017, 5 pages.

Jun et al., "Automatic Calibration of Frequency Compensation System in Computer-Controlled Patch-Clamp Amplifier", Journal of Computer Science, vol. 3, No. 10, Oct. 1, 2007, pp. 765-772.

PCT/US2016/051328, "International Search Report and Written Opinion", dated Jan. 10, 2017, 17 pages.

PCT/US2016/051328, "Invitation to Pay Additional Fees and Partial Search Report", dated Nov. 15, 2016, 5 pages.

Sigworth, "Design of the EPC-9 A Computer-Controlled Patch-Clamp Amplifier. 1. Hardware", Journal of Neuroscience Methods, vol. 56, Issue 2, Feb. 1995, pp. 195-202.

Weerakoon et al., "An Integrated Patch-Clamp Potentiostat With Electrode Compensation", IEEE Transactions on Biomedical Circuits and Systems, IEEE, US, vol. 3, No. 2, Apr. 1, 2009, pp. 117-125.

Sophion Bioscience, webpage: http://sophion.com/knowledgecenter/publications/?fwp_publications_type=poster; retrieved Jan. 16, 2018; 19 pages.

Sophion Bioscience, Inc.; "Clip Detecting" with Series Resistance Compensation Using an Automated Patch Clamp System; 1 page; retrieved Jan. 16, 2018 via webpage: http:// so phi on. com/wp-content/uploads/2017/03 /Po st er_ Clip-detecting-with-series-resistance-compensationusing-an-automated-patch-clamp-system-handout.pelf.

A. V Oppenheim et. al, "Discrete-Time Signal Processing 2nd Ed", p. 442-465, 1989, Prentice-Hall Inc.,New Jersey.

L.A Lojkner et. al, "Clip detecting with series resistance compensation using an automated patch clamp system", Poster presented at 56th Biophysical Meeting, Feb. 25-29, 2012, San Diego CA.

"Bilinear Transform", Wikipedia entry at Wayback Archive https:/web.archive.org/web/20140912114736/https://en.wikipedia.org/wiki/Bilinear_transform, Sep. 13, 2014.

"Digital Filter", Wikipedia entry at Wayback Archive https://web.archive.org/ web/20140603223921/en.wikipedia.org/wiki/Digital_filter, Jun. 3, 2014.

F.J. Sigworth, "Design of the EPC-9 A computer-controlled patch-clamp amplifier 1. Hardware", J. Neu rosci. Methods vol. 56 p. 195-202, 1995.

F.J. Sigworth, "Single-Channel Recording" 2nd Ed p. 95-127, 1995, Springer Science and Business Media LLC, New York.

Communication Relating to the Results of the International Search (Annex to Form PCT/ISA/206) dated Nov. 15, 2016, International Appl. No. PCT/US2016/051328.

Prinz et al., Dynamic clamp, Scholarpedia, 6(5):1470 (2011) (downloaded on Aug. 3, 2016 from http://www.scholarpedia.org/article/Dynamic_clamp).

Xiong et al., Automatic Calibration of Frequency Compensation System in Computer-Controlled Patch-Clamp Amplifier, Journal of Computer Science 3 (9): 765-772, 2007.

Scouten Charles; Neuroscience Tools, Introducing Digital Clamp One Electrophysiology Clamping Amplifier, Neuroscience Tools, 4 pages.

Molecular Devices, "The Axon Guide, Electrophysiology and Biophysics Laboratory Techniques", third edition, 1-2500-0102 D, Feb. 2012, 302 pages.

Axon Instruments Inc., "Axopatch 200B Patch Clamp Theory and Operation" Part No. 2500-121, Rev D, Mar. 1999, sections 75-101., 153 pages.

Notice of Allowance received in U.S. Appl. No. 14/859,227, dated Apr. 5, 2019; 14 pages.

DIGITAL PATCH-CLAMP AMPLIFIER

CROSS-REFERENCES TO RELATED APPLICATIONS

This application is a continuation-in-part of U.S. patent application Ser. No. 14/859,227, filed Sep. 18, 2015, which is incorporated by reference.

BACKGROUND

Patch-clamp amplifiers may be used in cellular and molecular biology to measure and record electrical signals generated by biological tissue. Biological tissue may allow a small current to flow through a cell wall or membrane when the cell is stimulated with a voltage signal. Simply put, patch-clamp amplifiers may be used to measure and record a resulting current that flows through a cell as a result of a voltage input. Typically, the voltage input is a step or other function, referred to as a command signal, which may be applied via a pipette that is in contact with the cell. A resulting current may then be measured and recorded.

It can be very difficult to measure and record this resulting cell current. For example, the pipette may have a stray or parasitic capacitance that may generate a large current when the command signal is applied. This large signal may swamp or overwhelm the desired output signal current generated by the cell, thereby making a determination of the actual cell current problematic. Similarly, the pipette and cell may have other stray or parasitic capacitances and resistances and the current signals they produce may similarly hide or mask the current of interest, specifically the current generated by the cell itself.

The solution has been to include various circuits in these patch-clamp amplifiers that compensate for these unwanted signals, thereby leaving the desired signals behind. But this has led to patch-clamp amplifiers having a tremendous complexity. These complex patch-clamp amplifiers have proven to be difficult to manufacture. Further, they have become so specialized that once made, they may be very difficult to reconfigure. For example, it may be desirable to reconfigure one or more circuits in a product update or improvement. The complexity of present patch-clamp amplifiers may limit such reconfiguration.

Moreover, during device use, it may be desirable to quickly reconfigure a patch-clamp amplifier in order to take a set of related measurements. Again, the complexity of present patch-clamp amplifiers may slow the reconfiguration process and limit the ability to take such related measurements.

Thus what is needed are patch-clamp amplifiers that may be readily manufactured, may be simple to reconfigure for product updates, and can be quickly reconfigured into different modes during operation.

SUMMARY

Accordingly, embodiments of the present invention may provide patch-clamp amplifiers that may be readily manufactured, may be simple to reconfigure for product updates, and can be quickly reconfigured into a different mode during operation.

An illustrative embodiment of the present invention may provide patch-clamp amplifiers that may be readily manufactured by implementing some or all of the compensation and other circuits in a patch-clamp amplifier using digital circuitry. These digital circuits may be implemented using discrete or integrated logic circuits, programmable logic such as field-programmable gate arrays or programmable logic arrays, microprocessors, or other fixed or configurable logic circuits or a combination thereof. These digital circuits may replace complicated analog circuits that may have several limitations and undesirable characteristics. For example, these analog circuits may require the manual tuning or adjustment of several potentiometers and other variable components. These adjustments may inadvertently become altered or lost when the patch-clamp amplifier is subjected to force, for example during shipment. Also, the potentiometers themselves may be relatively expensive or difficult to procure due to a lack of present-day demand for such components. The use of digital circuitry to replace this complicated analog circuitry may provide patch-clamp amplifiers that are more readily manufactured.

More specifically, embodiments of the present invention may provide a patch-clamp amplifier having a headstage circuit to receive an input signal, which may be referred to as a command signal, to receive a current signal resulting from the command signal, and to convert the received current signal to a voltage. The patch-clamp amplifier may further include one or more compensation circuits to compensate for various non-ideal aspects of a measurement system that includes the patch-clamp amplifier. The patch-clamp amplifier may have other circuits to boost a gain of the headstage, filter an output, or perform other functions. In various embodiments of the present invention, the headstage circuit may be implemented using analog circuitry, while at least one of the one or more compensation and other circuits maybe implemented using digital circuitry. Analog-to-digital converters (ADCs) and digital-to-analog converters (DACs) may be used to convert signal between the headstage circuit and the one or more compensation and other circuits. These converters may be located close to the headstage to reduce noise coupling on the analog signal lines.

An illustrative embodiment of the present invention may further provide patch-clamp amplifiers that may be simple to reconfigure for product updates. In various embodiments of the present invention, at least one of the one or more compensation and other circuits may be implemented using programmable logic circuits. These programmable logic circuits may be reconfigured by a user or by a manufacturer through firmware or software updates. This may provide a simple reconfiguration, particularly when compared to what would otherwise be needed to reconfigure a complicated analog circuit involving many separate gain circuits, switches, capacitors, and the like.

This configurability may also be advantageous during the operation of a patch-clamp amplifier. For example, an illustrative embodiment of the present invention may provide a patch-clamp amplifier that may operate in various modes, including a voltage-clamp mode and a current-clamp mode. It may be useful if the patch-clamp amplifier can alternate or switch from one of these modes to the other, or switch between them-in rapid succession. Again, while this may be difficult to implement in conventional patch-clamp amplifiers, the patch-clamp amplifier provided by the illustrative embodiment may implement key pathways involved in this mode switch using programmable logic. This programmable logic may be quickly reconfigured to allow rapid changes between modes.

The use of programmable logic or other digital circuitry for the one or more compensation or other circuits may provide performance improvements as well. For example, operation amplifiers may produce non-linear or non-symmetrical responses, time delays, excess noise, and they may have bandwidth limitations and be subject to temperature drift. Capacitors may exhibit non-ideal properties such as leakage and dielectric absorption. Analog switches may have considerable ON resistance, non-linearities, and suffer from crosstalk. Replacing these components with programmable logic or other digital circuits may provide compensation and other circuits that have improved performance.

Another illustrative embodiment of the present invention may provide a patch-clamp amplifier having a headstage. The headstage may receive a command signal, provide the command signal to a cell, receive a resulting current, convert the resulting current to an output voltage, and provide the output voltage. The headstage may include a trans-impedance or other type of amplifier. Specifically, the command signal may be received at a first input terminal of a trans-impedance amplifier. The trans-impedance amplifier may have feedback configured such that a voltage on a second input terminal of the trans-impedance amplifier follows the command signal applied to the first input terminal. This voltage may then be provided to a cell. A resulting current may be received at the second input terminal. The current may flow through a feedback impedance around the trans-impedance amplifier to generate a voltage, which may be provided as an output.

There may be several parasitic components in a measurement system that includes this patch-clamp amplifier. These parasitic components may generate signals that may mask a desired current signal generated by a cell. Several of these parasitic components may produce signal components that may be compensated for by compensation circuits in the patch-clamp amplifier. One or more of these compensation circuits may be implemented using programmable logic or other digital circuitry. A specific embodiment of the present invention may provide a patch-clamp amplifier where each of these compensation circuits is implemented on a programmable logic circuit. Each of these compensation circuits may at least reduce or mitigate an unwanted signal component. Each may do so by providing a countervailing signal. At least some of these countervailing signals may be provided by digital-to-analog converters that convert countervailing signals from the programmable logic circuit and provide analog signals to the headstage circuit.

In this and other embodiments of the present invention, one or more of these compensation circuits may include circuitry to adjust a magnitude and a frequency response of the countervailing signal such that it more accurately reduces or mitigates an unwanted signal component. In these embodiments, each compensation circuit may include a fixed or variable gain circuit to adjust the magnitude and a filter to adjust the frequency response of a countervailing signal. It should be noted that these gain circuits may provide a gain of less than unity and may therefore operate as an attenuator. These countervailing signals may be added to the command signal, they may be injected as currents that are added to the cell current, or they may be added either to the output signal or an amplified or filtered version of the output signal.

These parasitic components in a measurement system that may include a patch-clamp circuit according to an embodiment of the present invention may include a capacitance of a pipette, a resistance of the pipette, a capacitance of the cell, and a resistance of the cell. The resistance of the cell, the series resistance of the pipette, and capacitance of the cell may create a time constant that may act as a filter and may slow an edge of a step or other voltage applied to a cell. From the cell, the series resistance of the pipette and the cell resistance may be in parallel. Since the cell resistance may typically be much larger than the series resistance, the time constant can be simplified to be dependent on the cell capacitance and the series resistance. To reduce or mitigate this filtering, an embodiment of the present invention may employ a series resistance prediction circuit. This circuit may receive a step or other function, add an overshoot portion, and provide the sum as the command signal. The overshoot portion may help to reduce the delayed response that would otherwise be seen at the cell due to the time constant of the cell capacitance and series resistance. The series resistance prediction circuit, as with the other compensation circuits, may include a filter and a gain stage. Specifically, the series resistance prediction circuit may include a high-pass filter to provide the overshoot. The frequency response of the high-pass filter may be set by an estimation of the cell capacitance and series resistance. The series resistance prediction circuit may also include a gain stage. The series resistance prediction circuit may be an open loop path. That is, an estimate of the cell capacitance and series resistance may be used to generate a prediction signal that is added to the command signal.

The series resistance prediction circuit may also be used in a calibration routine to determine estimated values of the series resistance and the cell capacitance. For example, an initial estimation may be used to set the frequency response of the filter in the series resistance prediction circuit, which provides the overshoot signal to compensate for the limited bandwidth caused the time constant seen by the cell. The amount of compensation needed to compensate for the filtering effect of the series resistance and cell capacitance can be found. Specifically, the peak amplitude and time constant of the overshoot waveform needed can be found. From this, an estimation of the series resistance and the cell capacitance can be determined and used in the series resistance prediction circuit and elsewhere.

The series resistance may also cause a voltage drop that lowers the input voltage provided to the cell. Specifically, as the cell receives an input voltage and begins to conduct, the current may flow through the series resistance, thus lowering the voltage seen by the cell. To reduce or mitigate this, an embodiment of the present invention may employ a series resistance correction circuit. This circuit may receive an output from the headstage, and provide a correction voltage to the command signal. Specifically, since an estimation of the series resistance is known, as the headstage output increases, it can be determined how much of a voltage drop is being seen at the cell due to cell current passing through the series resistance. The command signal, and thus the input voltage, can be increased to compensate and to help maintain the voltage seen by the cell. Since the output of the headstage is being used to generate an input to the headstage, the series resistance correction circuit is a closed loop circuit. To prevent this loop from oscillating, a lag filter may be used to limit the bandwidth of the feedback loop. This correction circuit may also include a gain circuit.

The pipette may have a capacitance associated with it. This capacitance may draw a charging current when an input voltage is applied to the pipette. Accordingly, an illustrative embodiment may inject a current at the input to compensate for this charging current. A pipette compensation path may be used to provide a voltage that is coupled through a capacitor to generate a voltage at the input node. The pipette compensation path may include a low-pass filter in series with a gain circuit. Specifically, the command signal may be received by the pipette compensation path. This signal may be low-pass filtered, which essentially integrates the command signal. The resulting voltage may be gained, or more specifically, attenuated. The output voltage may then be applied through a capacitor, which essentially takes the derivative of the output voltage and provides a current to the input. This current may then at least approximately cancel the current drawn by the pipette capacitance.

In various embodiments of the present invention, it may be desirable to model the pipette capacitance as a series of parallel capacitors coupled to each other through small resistors. In these embodiments of the present invention, a pipette compensation path may include parallel paths, each including a series combination of a low-pass filter in series with one or more gain circuits, in order to achieve a higher-order filter to compensate for the pipette capacitance more accurately.

In a similar way, the cell may have a capacitance associated with it. This capacitance may draw a charging current when an input voltage is applied to the pipette. Accordingly, an illustrative embodiment may inject a current at the input to compensate for this cell capacitance charging current. A whole-cell compensation path may be used to provide a voltage that is coupled through a capacitor to generate a current at the input node. The whole-cell compensation path may include a low-pass filter in series with a gain circuit. Specifically, a step or other function that is used to provide the command signal may be received by the whole-cell compensation path. This signal may be low-pass filtered, which essentially integrates the step or other function. The resulting voltage may be amplified an amount at least approximately equal to a ratio of the whole-cell capacitance to a coupling capacitor used to couple an output voltage of the whole-cell compensation path. The command signal itself may then be added to this signal to generate the output voltage of the whole-cell compensation path. The output voltage may then be applied through a capacitor, which essentially takes the derivative of the output voltage and provides a current to the input. This current may then at least approximately cancel the current drawn by the cell capacitance.

The series resistance and cell resistance may form a path to ground from the pipette input. This resistive path may thus create a leakage path that generates a leakage current. Accordingly, an embodiment of the present invention may employ a leakage subtraction circuit. The leakage current may increase the amplitude of the output voltage. Accordingly, the leakage subtraction circuit may receive the step or other function that is used to generate the command signal. The step or other function may be attenuated and subtracted from the output voltage to compensate for the increase in output amplitude caused by the leakage current.

These and other embodiments of the present invention may provide other circuits that may also be implemented using programmable logic or other digital circuitry. For example, it may be desirable to boost or gain an output signal from a headstage. It may also be desirable to filter the output of the headstage. Accordingly, a frequency boost that may include a filter and an optional gain stage may be inserted at an output of the headstage circuit. In these and other embodiments of the present invention, further filtering of the output signal may be desired. Accordingly, a signal conditioning filter, which may be implemented as a high-order Bessel or other type of filter, may be used to filter the output signal. This filter may have an adjustable bandwidth in various embodiments of the present invention.

Various embodiments of the present invention may utilize various control circuits. These control circuits may include a micro-controller or other processing circuit, a host computer, or other processing, controlling, or computing circuit. In an illustrative embodiment of the present invention, a micro-controller may be used to control programmable logic such as a field-programmable gate array. The microcontroller, or control circuitry on the programmable logic or elsewhere, may load configuration data for the programmable logic at start-up, reset, or other appropriate times. The microcontroller may be used to pass gain settings, filter constants, or other values to the programmable logic. In a specific example, a user may input a bandwidth for a filter into a host computer using a graphical user interface (GUI.) The microcontroller may fetch the bandwidth value from the host and calculate the needed filter constants. The filter constants may then be sent to the programmable logic, which may then configure the filter. In these and other embodiments of the present invention, the filter constant calculations may be done using double-precision floating point math.

In the above examples, a voltage is forced onto a cell and a resulting current is measured. This may be referred to as the voltage clamp configuration. In other test configurations consistent with embodiments of the present invention, a current is forced into a cell and the resulting voltage is measured. This may be referred to as the current clamp configuration. In these embodiments of the present invention, the circuitry may be reconfigured from the above-described voltage clamp configurations into a current clamp circuit. That is, the current clamp circuit may use the same circuits as used in the above examples, but reconnected into this new configuration.

Specifically, a command waveform may be received and converted to a current. The current may be forced into the cell and a resulting voltage may be gained and provided as an output. The pipette capacitance may be compensated for with a loop that gains a portion of the output voltage and applies it to the summing node via a capacitor. This technique may be referred to as capacitance neutralization. The series resistance may be compensated for by subtracting a portion of the command signal from the resulting output signal.

In other embodiments of the present invention, a changing current may be forced into a cell, where the current is changed over time such that a desired conductance as a function of time may be provided to a sample. This may be referred to as a dynamic clamp or conductance clamp configuration. The circuitry described above for the voltage clamp circuit, which may be reconfigured for a current clamp circuit, may be also be reconfigured into a conductance clamp, which may be more commonly referred to as a dynamic clamp. These embodiments of the present invention may vary the current and voltage conditions applied to a sample. This may be done to mimic the current and voltage conditions that one cell may provide to an adjoining cell, or for other reasons.

In a conductance clamp configuration, a desired or target conductance waveform may be received and stored in memory. A command signal having a first amplitude may be generated. The command signal may be used to generate a current into a sample. A resulting voltage may be measured. From this, a measured conductance may be calculated. A target conductance value may be read from memory, where the target conductance value is a target value of conductance at a next point in time. The measured conductance may be compared to the target conductance. The difference between the measured conductance and the target conductance may be used to determine a change in magnitude of the command signal amplitude.

In these and other embodiments of the present invention, the signals in an amplifier or measurement system may be converted between analog and digital at various locations in different signal paths. Instead of adding a digital command signal to a filtered and amplified digital signal to generate a whole-cell compensation signal, an analog version of the command signal may be added to an analog version of the filtered and amplified digital signal. For example, as before, a whole-cell compensation path may provide a voltage that is coupled through a capacitor to generate a current at the input node. The whole-cell compensation path may include a low-pass filter in series with a gain circuit. Specifically, a step or other function that is used to provide the command signal may be received by the whole-cell compensation path. This signal may be low-pass filtered, which essentially integrates the step or other function. The resulting voltage may be amplified an amount at least approximately equal to a ratio of the whole-cell capacitance to a coupling capacitor used to couple an output voltage of the whole-cell compensation path. This signal may be converted to an analog signal. An analog version of the command signal may then be added to this signal to generate the output voltage of the whole-cell compensation path. The output voltage of the whole-cell compensation path may then be applied through a capacitor, which may be referred to as a whole-cell capacitor, that essentially takes the derivative of the output voltage and provides a current to the input. This current may then at least approximately cancel the current drawn by the cell capacitance.

Unfortunately, this whole-cell capacitor may inject noise into the input node. Accordingly, these and other embodiments of the present invention may digitally subtract the output of the whole-cell compensation path from the headstage output signal before providing the resulting signal to the series resistance correction and prediction circuit. This may allow the removal of the whole-cell capacitor and its attendant noise.

Various embodiments of the present invention may incorporate one or more of these and the other features described herein. A better understanding of the nature and advantages of the present invention may be gained by reference to the following detailed description and the accompanying drawings.

DESCRIPTION OF ILLUSTRATIVE EMBODIMENTS

Figure 1:
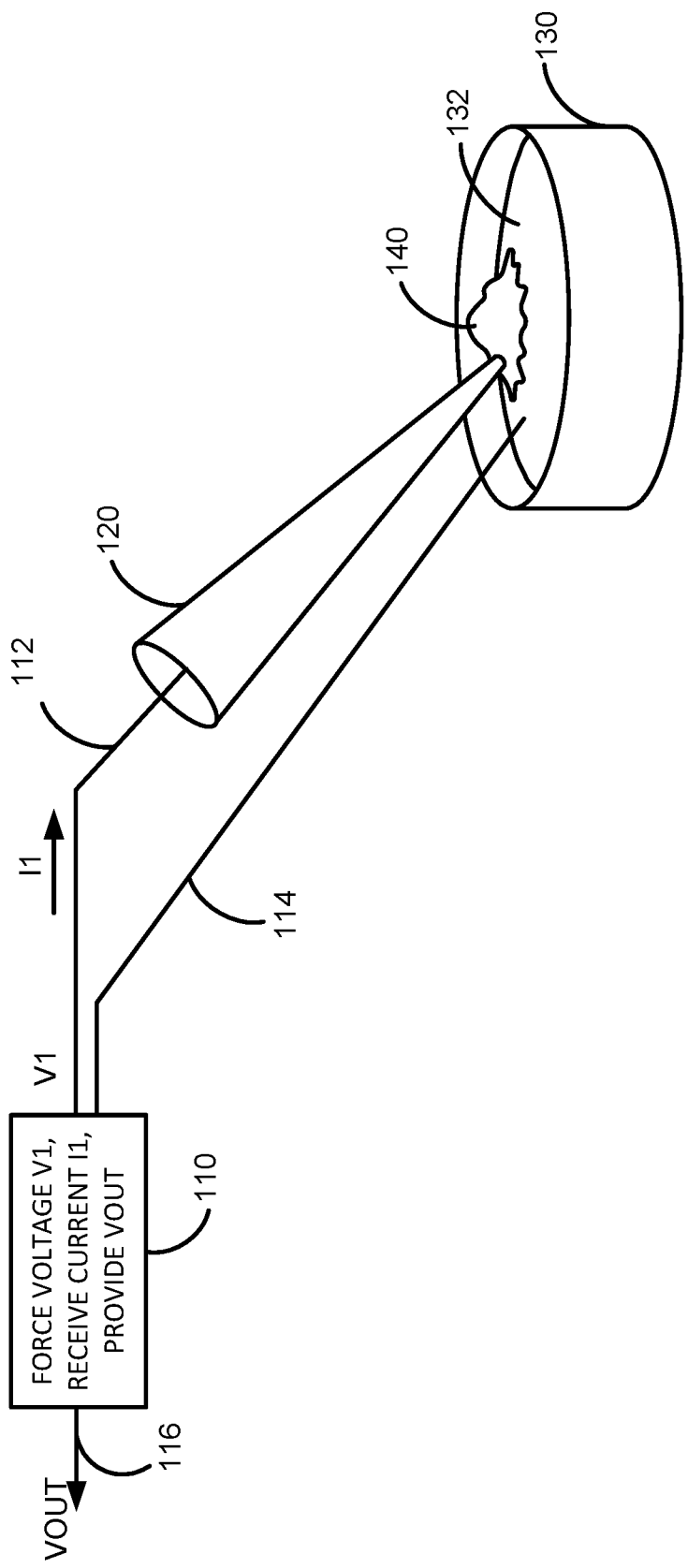
FIG. 1 illustrates measurement system that may be improved by the incorporation of an embodiment of the present invention.

FIG. 1 illustrates a measurement system that may be improved by the incorporation of an embodiment of the present invention. This figure, as with the other included figures, is shown for illustrative purposes and does not limit either the possible embodiments of the present invention or the claims.

This figure illustrates an amplifier 110 that may be used to characterize electrical responses of cell membrane, tissue, or sample 140. Specifically, one or more cells of a sample 140 may be placed in a bath 132 in a sample dish 130. Sample dish 130 may be a Petri dish or other type of sample dish. Amplifier 110 may provide voltage V1 via conductor 112 and pipette 120 to cell sample 140. Voltage V1 may be applied on conductor 112 relative to conductor 114, which may be in electrical contact with the bath 132. Bath 132 and conductor 114 may be electrically connected to ground.

As a signal voltage V1 is applied, a resulting current I1 may be provided by amplifier 110 to the cell sample 140. The provided current I1 may be converted to a voltage and provided as an output VOUT on line 116. The resulting voltage VOUT for a given input voltage V1 may be used to characterize electrical properties of cells in sample 140.

Unfortunately, several complications may arise when implementing this measurement system. For example, the resistance of the cells in sample 140 may be very high, and therefore any resulting current I1 may be very small and difficult to measure accurately. This may be further complicated by the presence of parasitic components in the pipette 120 and sample 140, as well as elsewhere in the measurement system. For example, pipette 120 may have resistances and capacitances associated with it. Cells in sample 140 may have resistances and capacitances associated with them as well. These parasitic components may act to distort voltage V1 before it is applied to sample 140, thereby degrading any resulting measurement. These parasitic components may also generate currents that may add to or even overwhelm I1, further degrading any resulting measurement. Examples of these parasitic components are shown in the following figure.

Figure 2:
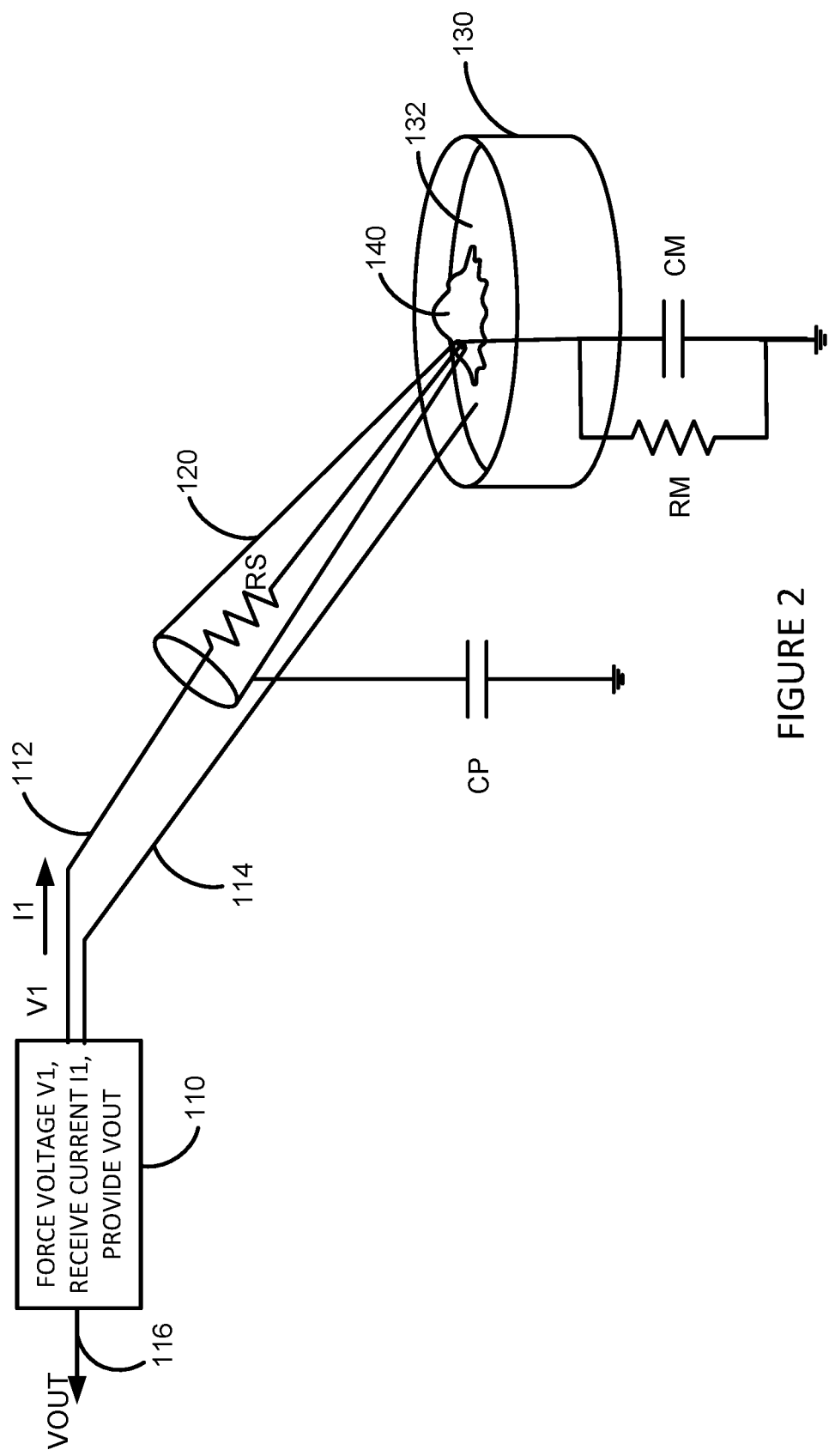
FIG. 2 illustrates parasitic components in a measurement system according to an embodiment of the present invention.

FIG. 2 illustrates parasitic components that may be present in a measurement system according to an embodiment of the present invention. In this figure, pipette 120 may have a series resistance RS. Pipette 120 may further have a parasitic capacitance CP to ground. Sample 140 may have a series resistance RM and a capacitance CM to ground or bath 132.

Again, these parasitic components may distort the voltage V1 as it is applied to sample 140. Also, these parasitic components may generate currents that may make the determination of I1 difficult. Accordingly, embodiments of the present invention may employ compensation circuits to compensate for these effects. For example, embodiments of the present invention may provide compensation circuits to adjust the voltage V1 such that a desired voltage is applied to the sample 140. These and other embodiments of the present invention may also provide compensation circuits to create currents to cancel the currents generated by the parasitic components.

Conventionally, such compensation circuits may be implemented with analog circuits. But these analog circuits may have several limitations and undesirable characteristics. For example, operational amplifiers may produce non-linear or non-symmetrical responses, time delays, excess noise, and they may have bandwidth limitations and be subject to temperature drift. Capacitors may exhibit non-ideal properties such as leakage and dielectric absorption. Analog switches may have considerable ON resistance, non-linearities, and suffer from crosstalk.

Also, these analog circuits may be difficult to manufacture. For example, these analog circuits may require the manual tuning or adjustment of several potentiometers and other variable components. These adjustments may inadvertently become altered or lost when the patch-clamp amplifier is subjected to force, for example during shipment. Also, the potentiometers themselves may be relatively expensive or difficult to procure due to a lack of present-day demand for such components.

Accordingly, embodiments of the present invention may provide patch-clamp amplifiers that may be readily manufactured by implementing some or all of the compensation and other circuits using digital circuitry. These digital circuits may be implemented using discrete or integrated logic circuits, programmable logic such as field-programmable gate arrays or programmable logic arrays, or other fixed or configurable logic circuits or a combination thereof. These digital circuits may replace these complicated analog circuits that may have several limitations and undesirable characteristics. The use of digital circuitry to replace this complicated analog circuitry may provide patch-clamp amplifiers that are more readily manufactured. Further, these programmable logic circuits may be reconfigured by a user or by a manufacturer through firmware or software updates. This may provide a simple reconfiguration, particularly when compared to what would otherwise be needed to reconfigure a complicated analog circuit involving many separate gain circuits, switches, capacitors, and the like. An example of a measurement system including these compensations circuits is shown in the following figure.

Figure 3:
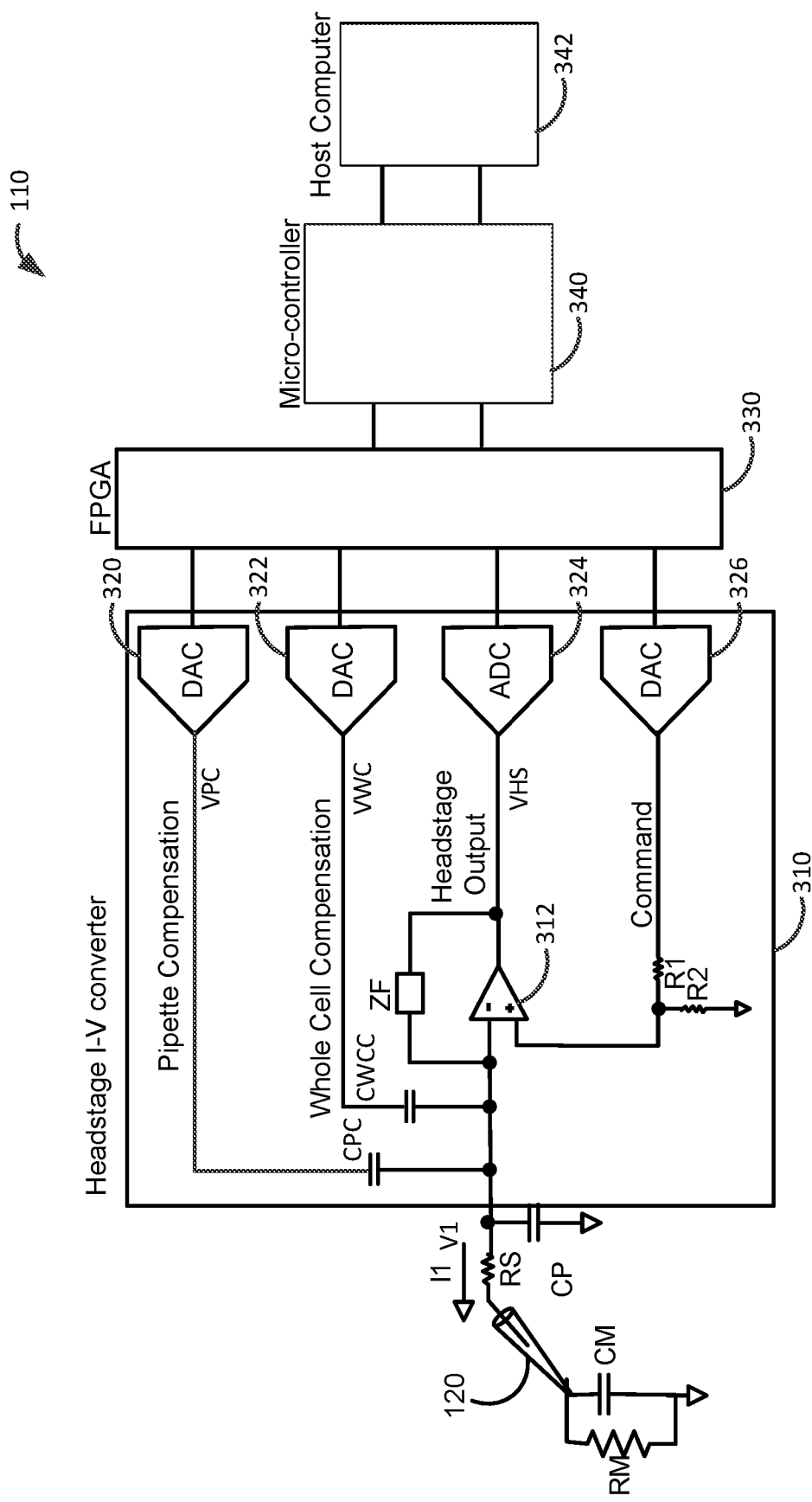
FIG. 3 illustrates a system diagram of a measurement system according to an embodiment of the present invention.

FIG. 3 illustrates a system diagram of a measurement system according to an embodiment of the present invention. This measurement system may include a headstage 310, field-programmable gate array (FPGA) 330, microcontroller 340, and a host computer 342. In this example, an amplifier, such as amplifier 110, may be implemented by headstage 310 and FPGA 330.

In this system, FPGA 330 may provide a digital function to digital-to-analog converter 326. Digital-to-analog converter 326 may convert the digital signal to an analog COMMAND signal. In this and other embodiments of the present invention, the digital function and the resulting COMMAND signal, may be a step, pulse, sine wave, ramp, saw-tooth, triangle wave, or other different or arbitrarily-shaped function. The analog COMMAND signal may be received at a non-inverting input of amplifier 312. Amplifier 312 may be configured as a trans-impedance amplifier. Amplifier 312 may drive voltage V1 such that it is equal to the analog command signal. The voltage V1 may be applied to membrane or sample 140 via pipette 120. The resulting current I1 may pass through feedback impedance ZF, thereby generating voltage VHS. The voltage VHS may be converted to a digital signal by analog-to-digital converter 324 and provided to the FPGA 330. In these and other embodiments of the present invention, FPGA 330 may be use to implement the synchronous digital hardware circuits disclosed herein.

Again, the parasitic components may degrade the signal V1 seen by the cell. Accordingly, FPGA 330 may provide a V1 that is pre-compensated such that the actual V1 seen by the cell is a desired waveform. Also, the parasitic components in this measurement system may create currents. These currents may be compensated for by embodiments of the present invention. In this example, FPGA 330 may provide a pipette compensation signal VPC via a digital-to-analog converter 320 to capacitor CPC. The voltage applied at capacitor CPC relative to V1 may generate a current to compensate for a current generated by the pipette capacitance CP. Similarly, the FPGA 330 may provide a whole-cell compensation signal VWC via digital-to-analog converter 322 to capacitor CWCC. The voltage applied at capacitors CWCC relative to V1 may generate a current to compensate for a current generated by the membrane capacitance of sample 140.

In this example, FPGA 330 may be controlled by microcontroller 340. Microcontroller 340 may be used to load configuration data into FPGA 330 at start-up, reset, or other appropriate times. The microcontroller 340 may also be used to pass gain settings, constants, or other variables or values to FPGA 330.

The host computer 342 may provide a user interface to the measurement system. In a specific example, a user may input a bandwidth for a filter into host computer 342 using a graphical user interface. Microcontroller 340 may fetch the bandwidth value from the host and calculate the needed filter constants. The filter constants may then be sent from the microcontroller 340 to the FPGA 330, which may then configure the filter.

In these examples, analog-to-digital and digital-to-analog converters may be used to convert signal between the headstage circuit and the one or more compensation and other circuits. These converters may be located close to the headstage to reduce noise coupling on the analog signal lines. In a specific example, the headstage 310 and converters 320-326 are in a first box or on a first board near the pipette 120 and sample 140, while the FPGA 330 is in a second remote box or on a second remote board, where one or more cables convey the digital information between the two.

In this example, the various compensation paths may be included in FPGA 330. In other block diagrams, they may be shown as distinct circuits. Examples are shown in the following figures.

Figure 4:
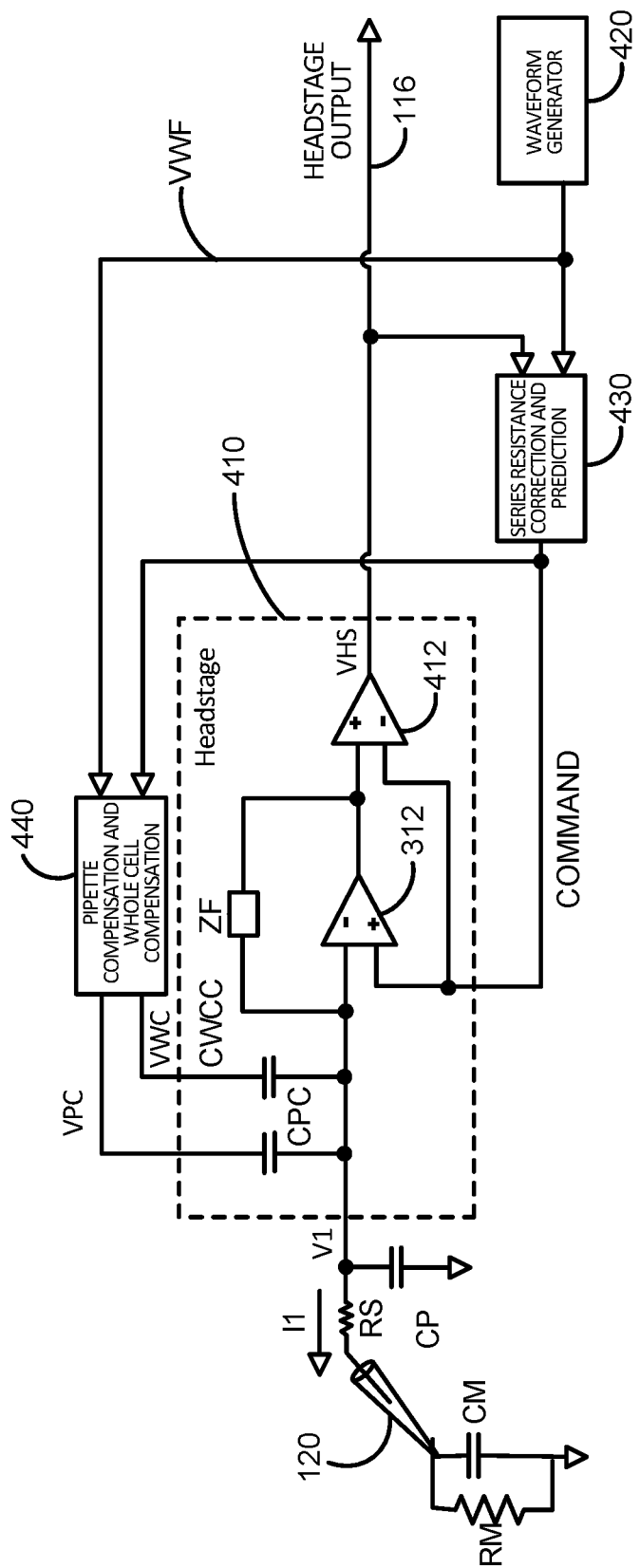
FIG. 4 illustrates another system diagram of a measurement system according to an embodiment of the present invention.

FIG. 4 illustrates another system diagram of a measurement system according to an embodiment of the present invention. In this example, an amplifier, such as amplifier 110, may be implemented using headstage 410, waveform generator 420, series resistance correction and prediction 430, and pipette compensation and whole-cell compensation 440. In various embodiments of the present invention, waveform generator 420, series resistance correction and prediction 430, and pipette compensation and whole-cell compensation 440 may be implemented using an FPGA or other programmable circuitry, such as FPGA 330. Waveform generator 420, series resistance correction and prediction 430, pipette compensation and whole-cell compensation 440, and the other digital circuits shown here may be implemented on an FPGA, such as FPGA 330, as synchronous digital hardware circuits.

The waveform generator 420 may generate a step or other function VWF to be applied to the cell membrane. Again, parasitic components may degrade the generated step or other function before it reaches the cell. Accordingly, a series resistance correction and prediction 430 may adjust this step or other function VWF and generate a COMMAND signal, which it may provide to headstage 410.

More specifically, the cell may see a capacitance CM in parallel with resistors RS and RM. Since the resistance RM of the membrane may be large, this parallel combination may be simplified to the capacitance CM and resistance RS. These components may effectively create a time constant at the cell membrane, which may have the effect of rolling off a leading edge of a step or other function applied to the cell. To compensate for this roll off, a boost or overshoot may be added to the waveform VWF generated by waveform generator 420 by the series resistance correction and prediction 430 to generate the COMMAND signal.

The COMMAND signal may be received by headstage 410, which may in turn generate the input voltage to the cell, V1. The step waveform V1 may generate a current through the pipette capacitance CP. To compensate for the current through capacitance CP, pipette compensation and whole-cell compensation 440 may receive the COMMAND signal and the step function VWF from waveform generator 420 and generate a voltage VPC at capacitor CPC. Similarly, the applied voltage at the cell may generate a current through capacitor CM. To compensate for the current in capacitor CM, the pipette compensation and whole-cell compensation 440 may also provide a voltage VWC to capacitor CWCC. The resulting current may help to reduce or cancel the current in the membrane capacitance CM.

In this specific example, a second amplifier 412 in headstage 410 may be used to subtract the command signal from the output of amplifier 312, since the COMMAND signal would otherwise be added to the output signal VHS. In other embodiments of the present invention, this subtraction function may be implemented digitally, for example in FPGA 330.

Figure 5:
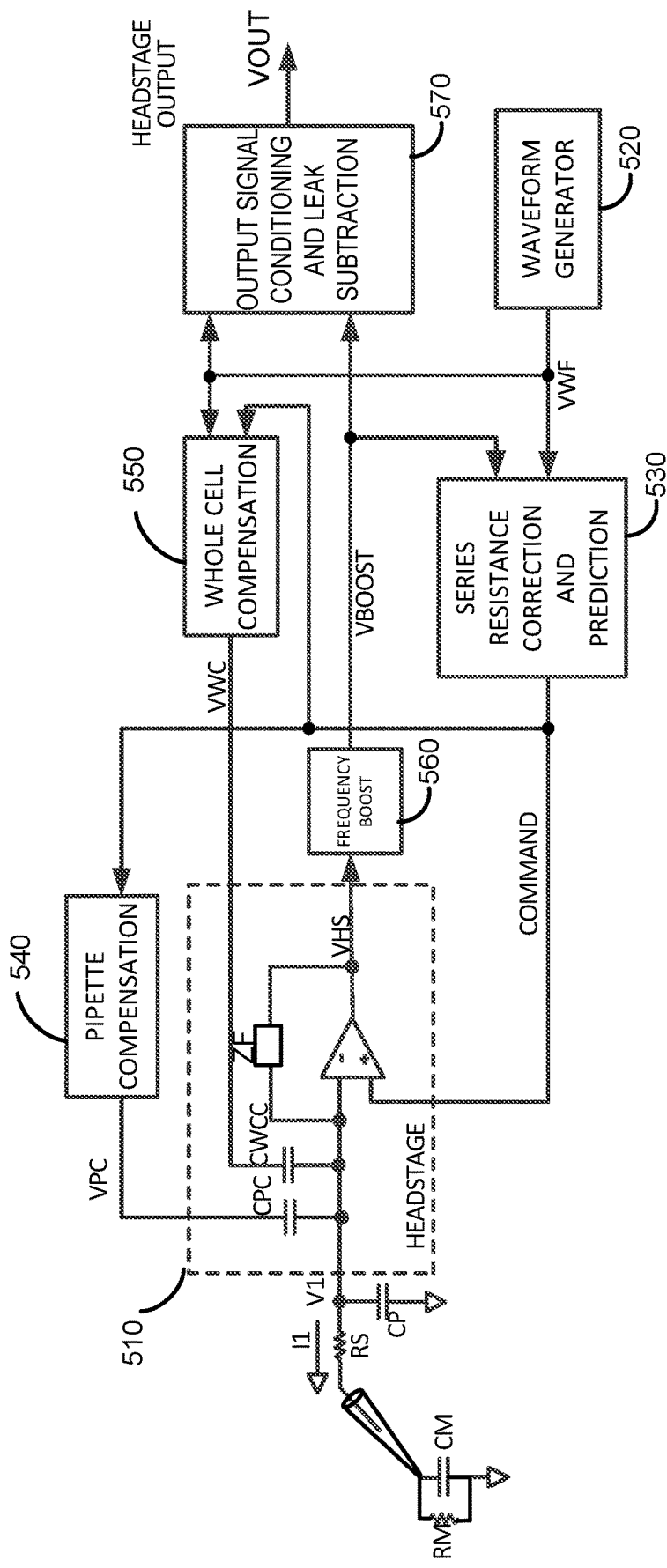
FIG. 5 illustrates another system diagram for a measurement system according to an embodiment of the present invention.

FIG. 5 illustrates another system diagram for a measurement system according to an embodiment of the present invention. In this example, pipette compensation 540 and whole-cell compensation 550 are shown as separate circuits. A frequency boost 560 and output signal conditioning and leak subtraction 570 have also been included. In this example, an amplifier, such as amplifier 110, may be implemented using headstage 510, waveform generator 520, series resistance correction and prediction 530, pipette compensation 540, whole-cell compensation 550, frequency boost 560, and output signal conditioning and leak subtraction 570. In one embodiment of the present invention, these circuits, except for headstage 510, may be implemented using digital circuitry, such as FPGA 330. Waveform generator 520, series resistance correction and prediction 530, pipette compensation 540, whole-cell compensation 550, frequency boost 560, output signal conditioning and leak subtraction 570, and the other digital circuits shown here may be implemented on an FPGA, such as FPGA 330, as synchronous digital hardware circuits.

As before, waveform generator 520 may generate a step or other function VWF. The waveform VWF may be received by series resistance correction and prediction 530. Series resistance correction and prediction 530 may generate a COMMAND signal, which may be received by headstage 510. Headstage 510 may receive the COMMAND signal and generate a voltage V1. Voltage V1 may be applied to a cell, with a resulting current I1. Current I1 may flow through feedback impedance ZF, thereby generating output voltage VHS. The output signal VHS may be amplified by frequency boost 560 to generate the signal VBOOST. The VBOOST signal may be received by the series resistance correction and prediction 530.

The COMMAND signal may be used by pipette compensation 540 to provide a voltage VPC. The voltage VPC may generate a current through capacitor CPC that may at least reduce or cancel a current in pipette capacitance CP. The COMMAND signal may also be provided to whole-cell compensation 550, which may also receive the output VWF from waveform generator 520. Whole-cell compensation 550 may generate a voltage VWC, which may be applied to capacitor CWCC. The voltage VWC may generate a current in capacitor CWCC that may at least reduce or compensate for current generated by capacitance CM at the membrane.

Output signal conditioning and leak subtraction 570 may receive the output signal VBOOST from frequency boost 560 and may filter VBOOST and provide it as an output VOUT. Output signal conditioning and leak subtraction 570 may also receive the output of waveform generator 520 and may compensate for the leakage path formed by the combination of the series resistance RS and cell membrane resistance RM.

As shown above, various configurations for the headstage may be used consistent with embodiments of the present invention. Examples are shown in the following figures.

Figure 6:
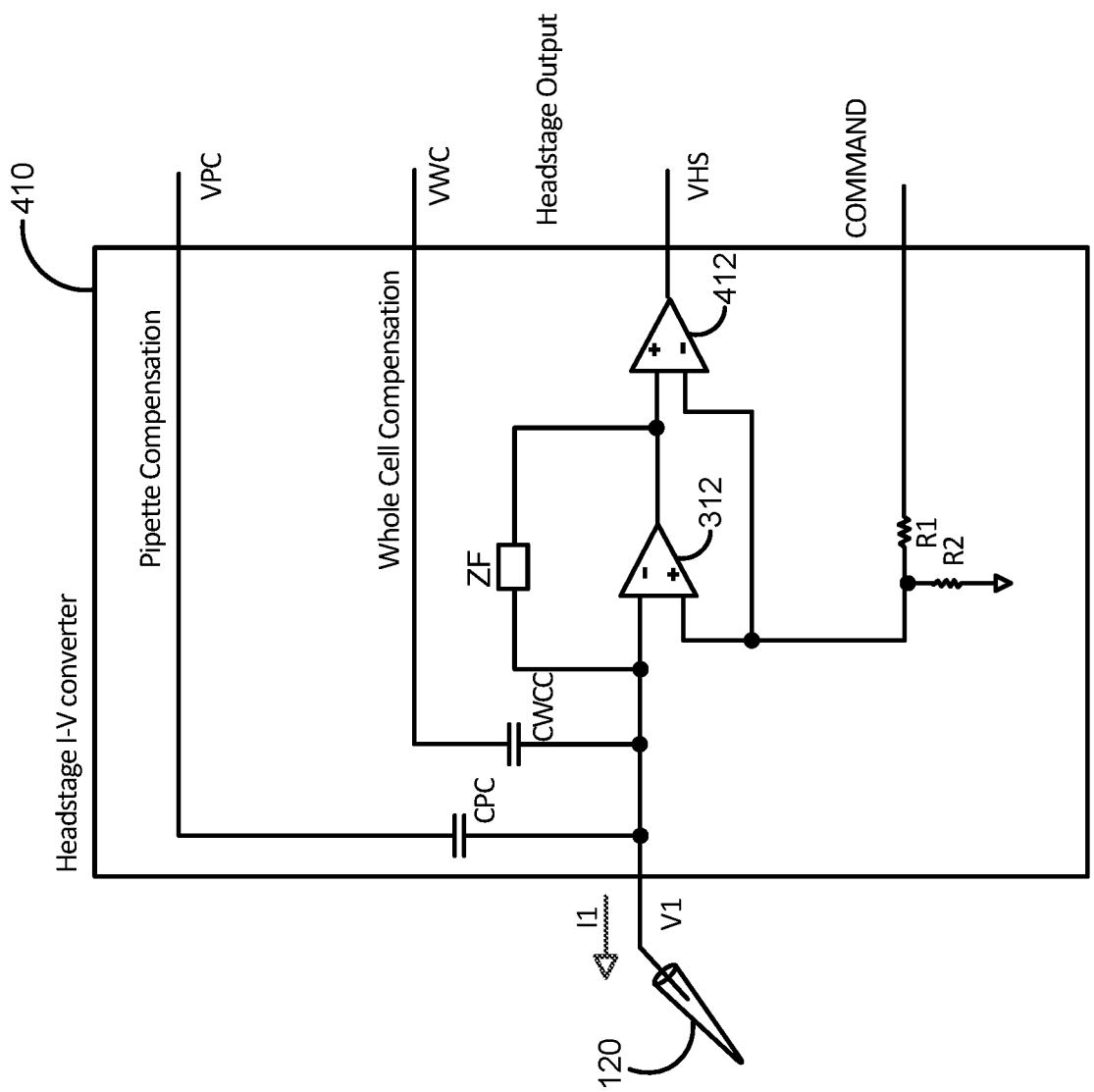
FIG. 6 illustrates a headstage according to an embodiment of the present invention.

FIG. 6 illustrates a headstage according to an embodiment of the present invention. As before, headstage 410 may receive a COMMAND signal. This COMMAND signal may be a step or other function with an overshoot, where the overshoot has been adjusted to compensate for an RC time constant at the cell sample. The COMMAND signal may be received at the non-inverting inputs of amplifier 312. The amplifier 312 may drive voltage V1 to track the COMMAND signal. V1 may be received by the cell and may generate a current I1. Current I1 may flow through feedback impedance ZF to create a signal at a non-inverting input of second amplifier 412. Second amplifier 412 may be configured to subtract the COMMAND signal from the resulting voltage and provide an output signal VHS.

A pipette compensation path may provide a voltage VPC to capacitor CPC, which may create a current to compensate for a current flowing in the pipette capacitance CP. A whole-cell compensation path may provide a voltage VWC to capacitor CWCC, which may create a current to compensate for a current flowing in the cell capacitance CM.

Figure 7:
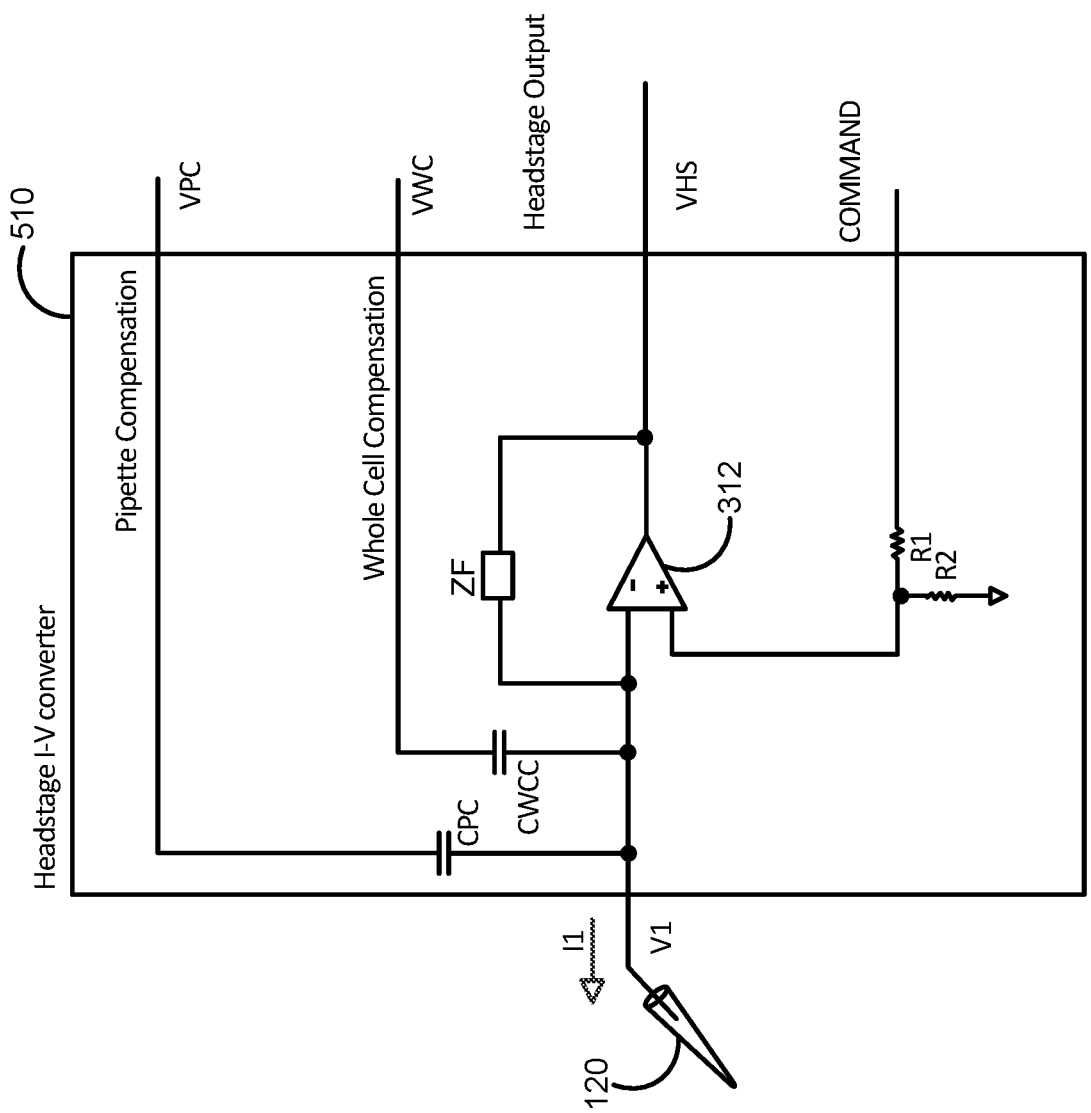
FIG. 7 illustrates another headstage according to an embodiment of the present invention.

FIG. 7 illustrates another headstage according to an embodiment of the present invention. In this example, the second amplifier 412 may be omitted, and the command signal may be digitally subtracted from the output signal VHS. An example of how this may be done is shown in the following figure.

Figure 8:
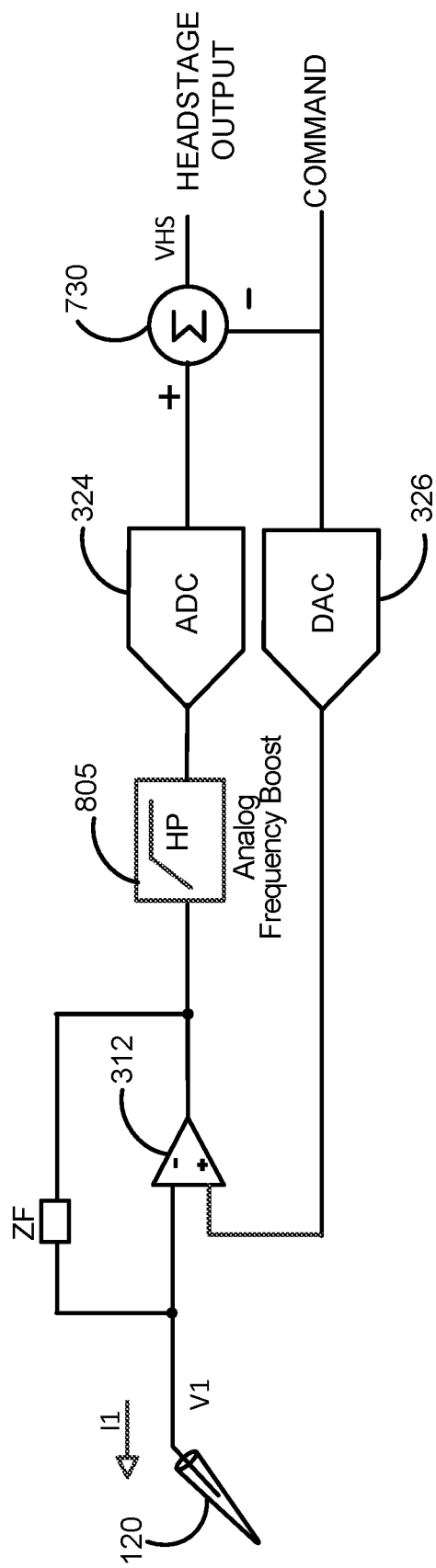
FIG. 8 illustrates a portion of a headstage and associated converters according to an embodiment of the present invention.

FIG. 8 illustrates a portion of a headstage and associated converters according to an embodiment of the present invention. In this example, a digital COMMAND signal may be received by digital-to-analog converter 326. Digital-to-analog converter 326 may provide the step or other function to a non-inverting input of amplifier 312. Amplifier 312 may drive V1 to the sample 140, thereby generating current I1. Current I1 may be generated a voltage across impedance ZF, which in this case may be a resistance. The output of amplifier 312 may be boosted using an analog frequency boost or high-pass filter 805. An analog-to-digital converter 324 may convert an output signal of the analog frequency boost or high-pass filter 805 to a digital signal. Summing node 730 may subtract the command signal from the output of analog-to-digital converter 324, thereby generating a headstage output voltage VHS.

Again, in this example, the feedback impedance ZF may be resistive. In other embodiments of the present invention, the feedback impedance ZF may be capacitive. When ZF is capacitive, the feedback capacitor ZF will integrate the current I1. To provide an output voltage, a digital frequency boost may be used. An example is shown in the following figure.

Figure 9:
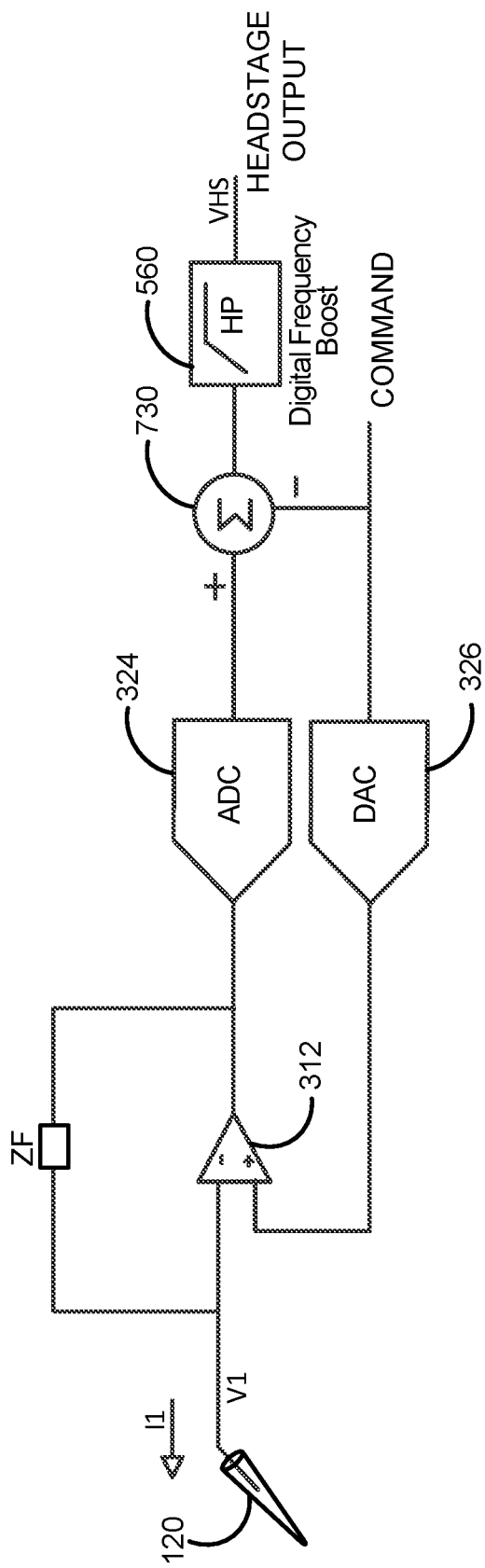
FIG. 9 illustrates a portion of a headstage and associated converters according to an embodiment of the present invention.

FIG. 9 illustrates a portion of a headstage and associated converters according to an embodiment of the present invention. Again, the COMMAND signal may be received by digital-to-analog converter 326. Digital-to-analog converter 326 may provide a step or other function to a non-inverting input of amplifier 312. Amplifier 312 may drive voltage V1 to follow this step or other function, thereby generating current I1. Current I1 may charge the capacitor that is the feedback impedance ZF, thereby generating a voltage, which may be converted by analog-to-digital converter 324. The command signal may be subtracted from the output of analog-to-digital convert 324 at summing node 730. The outputs of summing node 730 may be differentiated by digital frequency boost or high-pass filter 560 to provide an output signal VHS.

Figure 10:
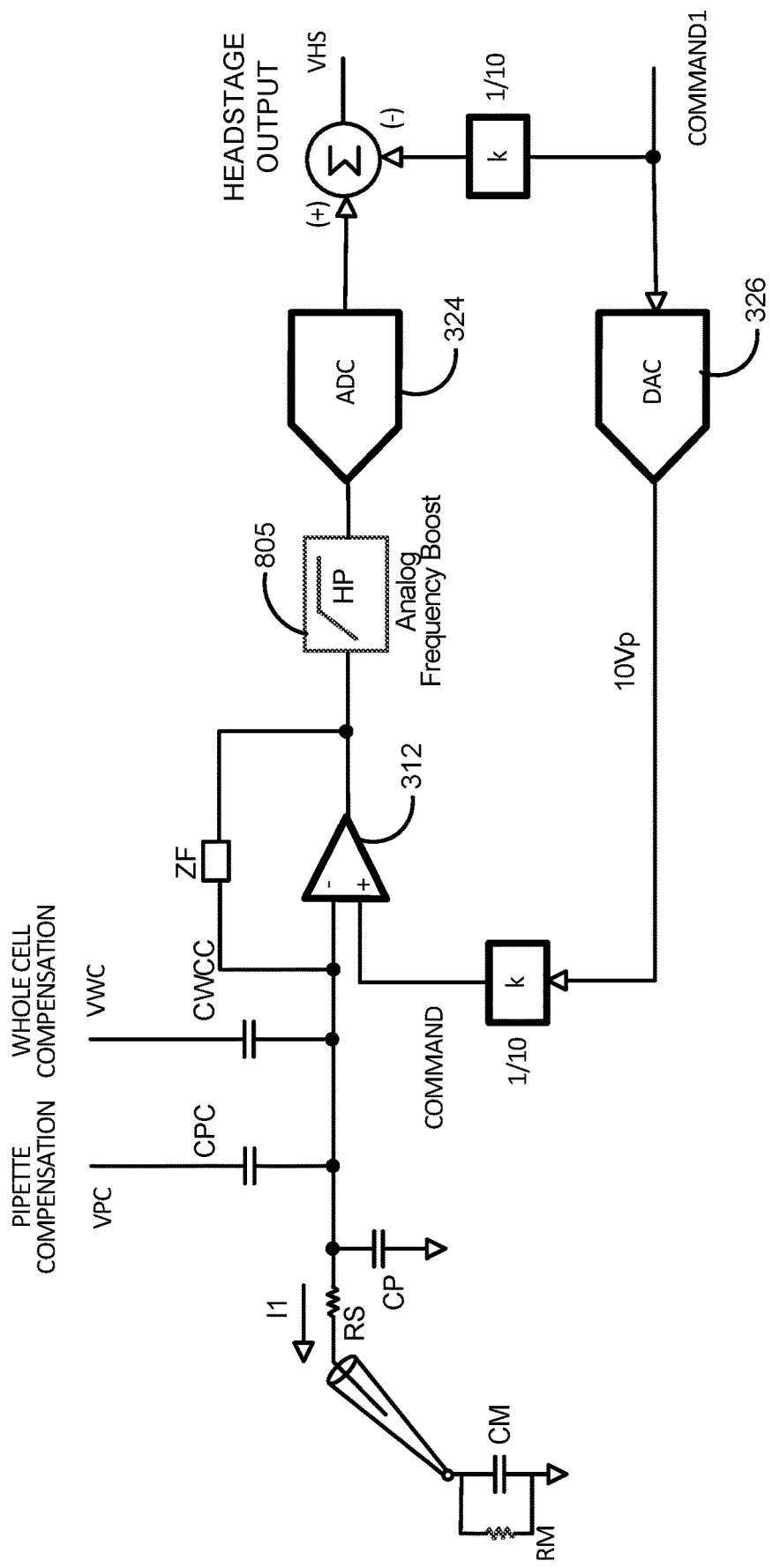
FIG. 10 illustrates another headstage according to an embodiment of the present invention.

FIG. 10 illustrates another headstage according to an embodiment of the present invention. In this example, the feedback component ZF may be resistive. As before, a COMMAND1 signal may be received by digital-to-analog converter 326. The digital-to-analog converter 326 may provide an output that is attenuated by a factor "k," which provides an analog COMMAND signal to a non-inverting input of amplifier 312. As before, amplifier 312 may drive V1 to follow the command signal. This may in turn generate a current I1, which may flow across impedance ZF, which may be a resistance, generating a voltage at an input of analog frequency boost or high-pass filter 805. An output of analog frequency boost or high-pass filter 805 may be received at an input of analog-to-digital converter 324. The command signal may be divided by a factor "k" and subtracted from the output of the analog-to-digital converter 324 to generate an upper voltage VHS.

In this example, attenuation blocks may provide attenuation factor of 0.1. This may allow the use of a larger dynamic signal as the COMMAND1 signal. This may provide a benefit in that more of the dynamic range of digital-to-analog converter 326 may be utilized and the quantization error of digital-to-analog converter 326 may be reduced by a factor of 10.

As before, capacitors CPC and CWCC may receive voltages to compensate for currents in capacitances CP and CM, respectively.

Figure 11:
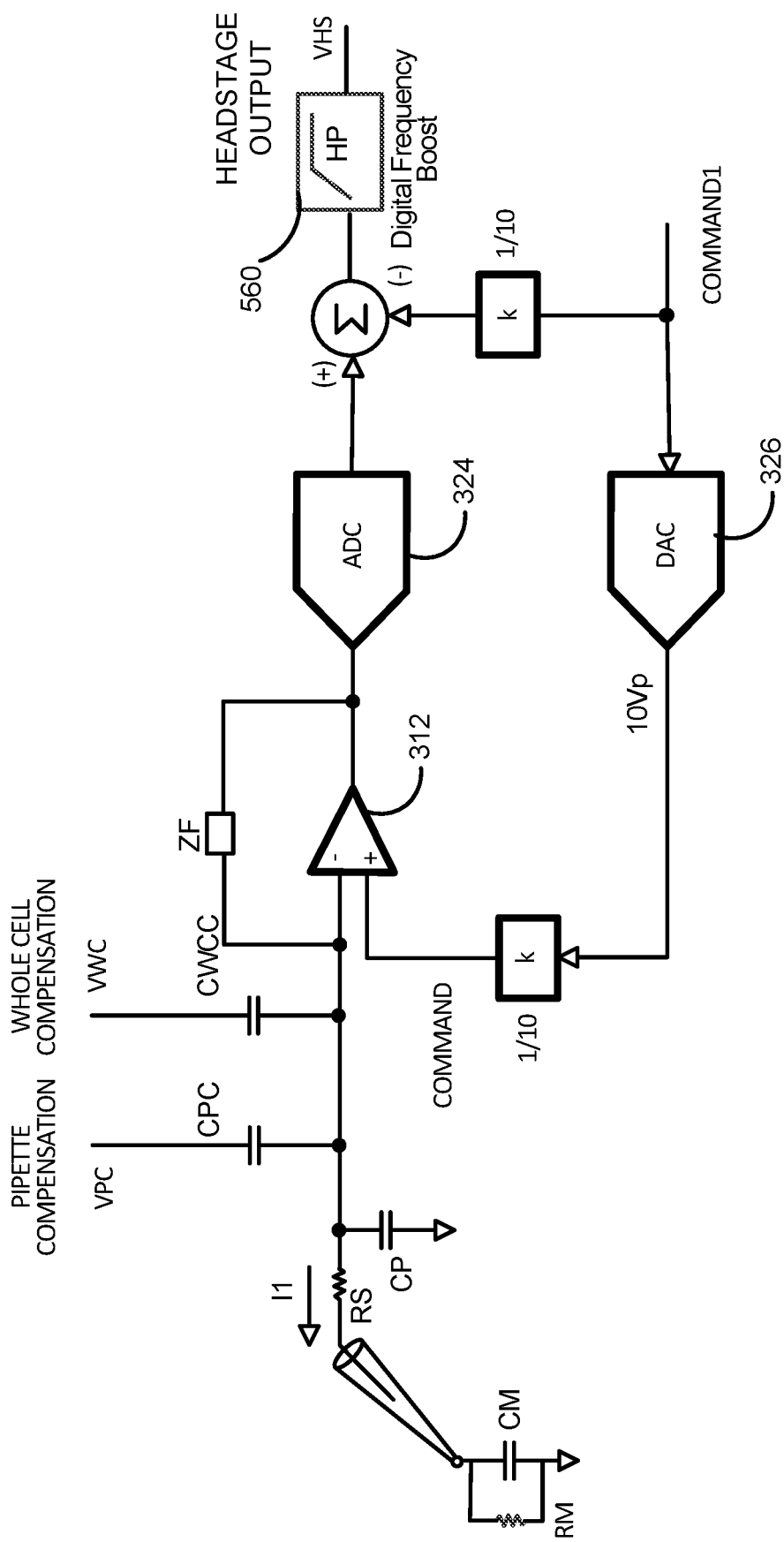
FIG. 11 illustrates another headstage according to an embodiment of the present invention.

FIG. 11 illustrates another headstage according to an embodiment of the present invention. In this example, feedback component ZF may be capacitive. Instead of passing the output of amplifier 312 through analog frequency boost or high-pass filter 805, the output of amplifier 312 may be converted to a digital signal by analog-to-digital converter 324. The output of analog-to-digital converter 324 may be summed with a gained portion of the COMMAND1 signal, where the gain may be an attenuation of approximately one-tenth. This attenuation may match the attenuation in the analog COMMAND path, making the attenuated COMMAND1 signal equal in amplitude, but in digital form, to the analog COMMAND signal applied to the inverting input of amplifier 312. The summed value may then be boosted by digital frequency boost or high-pass filter 560 before being provided as the output of the headstage.

Circuit blocks, such as the waveform generators shown above, may be implemented in various ways. Examples of waveform generators are shown in the following figures.

Figure 12:
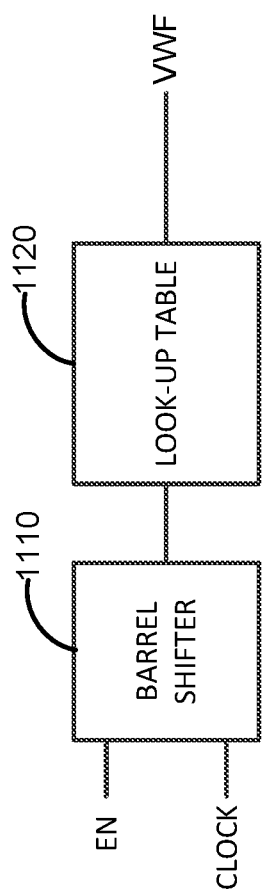
FIG. 12 illustrates a waveform generator according to an embodiment of the present invention.

FIG. 12 illustrates a waveform generator according to an embodiment of the present invention. This waveform generator may be used as a waveform generator, such as waveform generator 520, in various embodiments of the present invention. This waveform generator may include a barrel shifter 1110 and lookup table 1120. The barrel shifter 1110 may be enabled by enable signal EN and may be clocked by a clock signal CLOCK. The barrel shifter may act as a counter providing inputs to lookup table 1120. The desired step or other waveform function values may be stored in the lookup table 1120.

Figure 13:
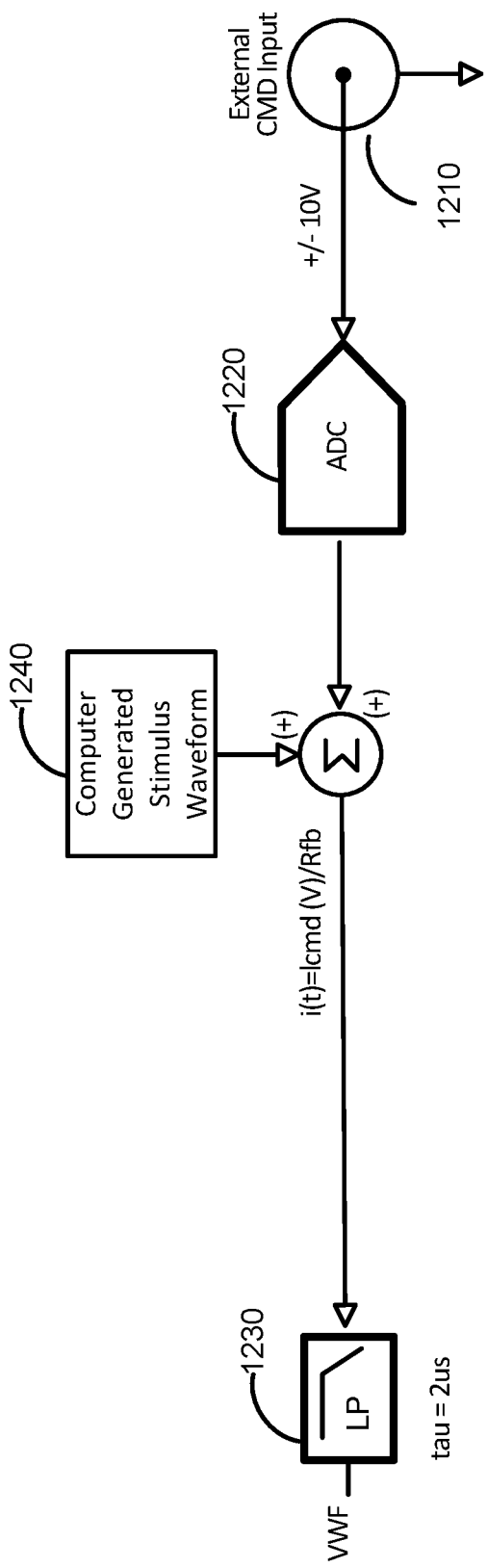
FIG. 13 illustrates another waveform generator according to an embodiment of the present invention.

FIG. 13 illustrates another waveform generator according to an embodiment of the present invention. In this example, at least two sources may be used to generate a waveform. The first is an external input 1210, which may receive a waveform from an external pulse or function generator. This waveform may be converted by analog-to-digital converter 1220 and provided to low-pass filter 1230. Low-pass filter 1230 may filter high-frequency edges of the waveform voltage and provide an output VWF.

The second source that may be used to generate a waveform is a waveform generator 1240. Waveform generator 1240 may provide an output to low-pass filter 1230, which may again provide waveform output VWF.

Again, these waveform generators may provide a step or other function to a cell. However, at the cell, this signal may be filtered by an RC time constant that includes the capacitance of the cell CM and the series resistance of the pipette RS. To compensate for this, an overshoot may be added to the step or other function. This compensating overshoot may be performed by a prediction circuit. Also, as a cell conducts current, a voltage may be generated across the series a resistance RS. To compensate for this voltage drop, the amplitude of the step or other function may be increased. This second compensation may be performed by a correction circuit. A series resistance correction and prediction circuit that may provide both functions is shown in the following figure.

Figure 14:
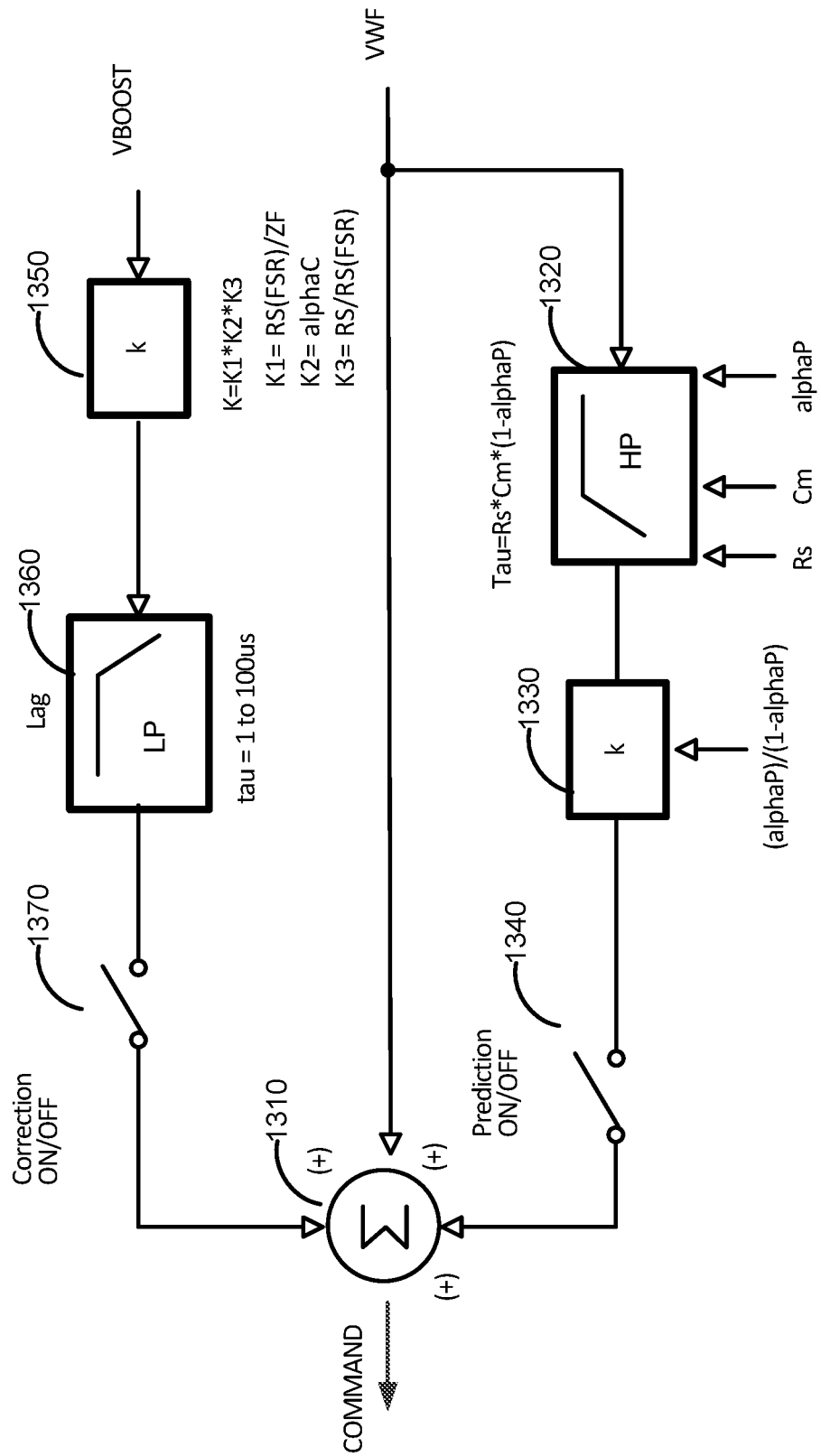
FIG. 14 illustrates a series resistance correction and prediction circuit according to an embodiment of the present invention.

FIG. 14 illustrates a series resistance correction and prediction circuit according to an embodiment of the present invention. This series resistance correction and prediction circuit may be used as the series resistance correction and prediction 530 and as other series resistance correction and prediction circuits in other embodiments of the present invention.

The step or other function VWF may be received from the waveform generator at summing node 1310. This waveform may also be filtered by high-pass filter 1320, which may generate an overshoot version of the waveform generator. The output of high-pass filter 1320 may pass through gain stage 1330 and be selectively added at summing node 1310. This path may be disabled by switch 1340. The overshoot version of VWF generated by high-pass filter 1320 may compensate for the RC time constant at the cell.

Again, as current begins to flow in the cell, a voltage may develop across the series resistance RS. This voltage may lower the voltage seen at the cell. Accordingly, an embodiment of the present invention may use a measurement of the cell current to increase the applied voltage at the cell, such that the applied voltage at the cell may remain at least approximately constant. In this example, the output signal VBOOST, which should be proportional to the cell current, may be gained by gain stage 1350 and filtered by filter 1360. This voltage may be added by summing node 1310 to create be command output signal. This path may be disabled by switch 1370.

It should be noted that each of the compensation paths included here are used to provide a voltage having a particular wave shape and amplitude. Accordingly, each compensation path may include a filter and a gain stage. Accordingly, the prediction path may include a high-pass filter 1320 and a gain stage 1330, while the correction path may include a filter 1360 and a gain stage 1350.

The series resistance prediction circuit may also be used in a calibration routine to determine estimated values of the series resistance and the cell capacitance. For example, an initial estimation may be used to set the frequency response of high-pass filter 1320. These settings may provide a magnitude and duration of the overshoot signal that is to compensate for the limited bandwidth caused by the time constant seen by the cell. The amount of compensation needed to compensate for the filtering effect of the series resistance RS and cell capacitance CM can be found by varying these estimates until the filtering effect is nulled. Specifically, the peak amplitude and time constant of the overshoot waveform needed to compensate for the cell time constant can be found. From this, an estimation of the series resistance and the cell capacitance can be determined and used in the series resistance prediction circuit and elsewhere.

It should be noted that the series resistance correction path is closed loop in nature. That is, a measurement of a cell current is used in real time to adjust an applied COMMAND signal and resulting V1. By comparison, the predication circuit is open loop since it receives or determines settings and uses the settings for following measurements with feedback adjustments.

Again, as an input voltage is applied to the cell, a current may flow in the cell capacitance. This capacitive current may be undesirable and may mask the true cell current. Accordingly, embodiments of the present invention may include a whole-cell compensation circuit to compensate for, or at least reduce, this cell capacitance current. An example is shown in the following figure.

Figure 15:
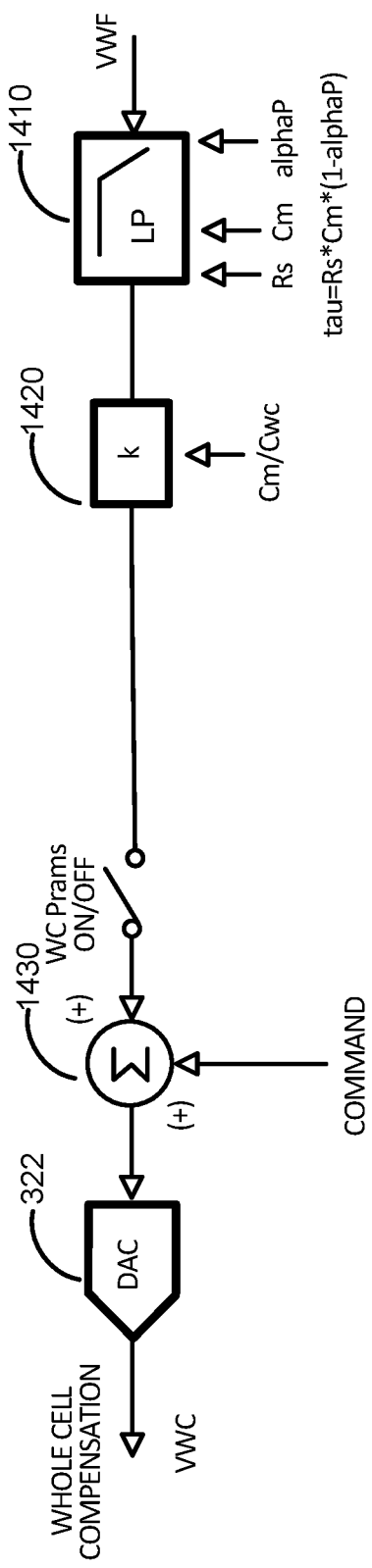
FIG. 15 illustrates a whole-cell compensation circuit according to an embodiment of the present invention.

FIG. 15 illustrates a whole-cell compensation circuit according to an embodiment of the present invention. A step or other function that is used to provide the command signal may be received by this whole-cell compensation path. This signal may be low-pass filtered, which essentially integrates the step or other function. The resulting voltage may be gained by a ratio of the whole-cell capacitance to a coupling capacitor used to couple an output voltage of the whole-cell compensation path. The command signal itself may then be added to this signal to generate the output voltage of the whole-cell compensation path. The output voltage may then be applied through a capacitor, which essentially takes the derivative of the output voltage and provides a current to the input. This current may then at least approximately cancel the current drawn by the cell capacitance.

Specifically, the waveform generator output signal VWF may be received at low-pass filter 1410. The output of the low-pass filter 1410 may be received by gain stage 1420. The output may be added to the COMMAND signal at summing node 1430 and provided to a digital-to-analog converter 322. Digital-to-analog converter 322 may generate a waveform VWC, which may be provided to capacitor CWCC, as shown above.

Again, as an input voltage is applied to the cell, a current may also flow in the pipette capacitance. This current may also be undesirable and may mask the true cell current. Accordingly, embodiments of the present invention may include a pipette compensation circuit to compensate for, or at least reduce, this pipette capacitance current. An example is shown in the following figure.

Figure 16:
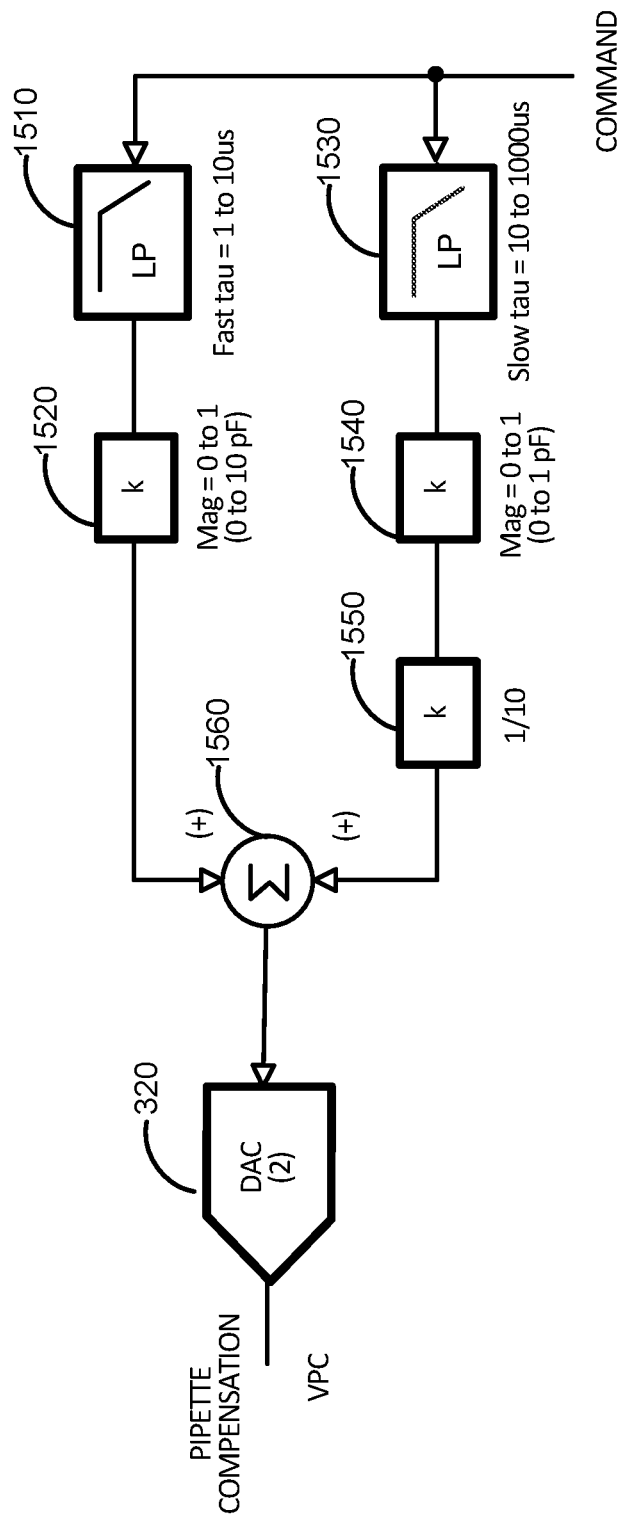
FIG. 16 illustrates a pipette compensation circuit according to an embodiment of the present invention.

FIG. 16 illustrates a pipette compensation circuit according to an embodiment of the present invention. The COMMAND signal may be received by the pipette compensation path. This signal may be low-pass filtered, which essentially integrates the COMMAND signal. The resulting voltage may be gained, or more specifically, attenuated. The output voltage may then be applied through a capacitor, which essentially takes the derivative of the output voltage and provides a current to the input. This current may then at least approximately cancel the current drawn by the pipette capacitance.

Specifically, the COMMAND signal may be received by low-pass filter 1510. The output of the low-pass filter 1510 may be gained or attenuated by gain stage 1520. The output of gain stage 1520 may be converted by digital-to-analog converter 320. Digital-to-analog converter 320 may provide an output voltage VPC to capacitor CPC as shown above. In various embodiments of the present invention, the pipette capacitance may be better approximated as two or three individual capacitors with small resistances between them. In such a case, more than one filter and gain stage series may be included. In this example, a second filter and gain stage including filter 1530 and gain stages 1540 and 1550 may also be included. The output of this additional stage may be summed with the output of gain stage 1520 at summing node 1560. In other embodiments of the present invention, further series combinations of the low-pass filters and gain stages may be included for better compensation of the pipette capacitance.

The series combination of RS as an RM may provide a leakage path from V1 to ground. This leakage path may be compensated for in order to reduce the resulting error this current may cause. Also, it may be desirable to filter the output signal. Accordingly, embodiments of the present invention may employ an output conditioning and leak subtraction circuit. An example is shown in the following figure.

Figure 17:
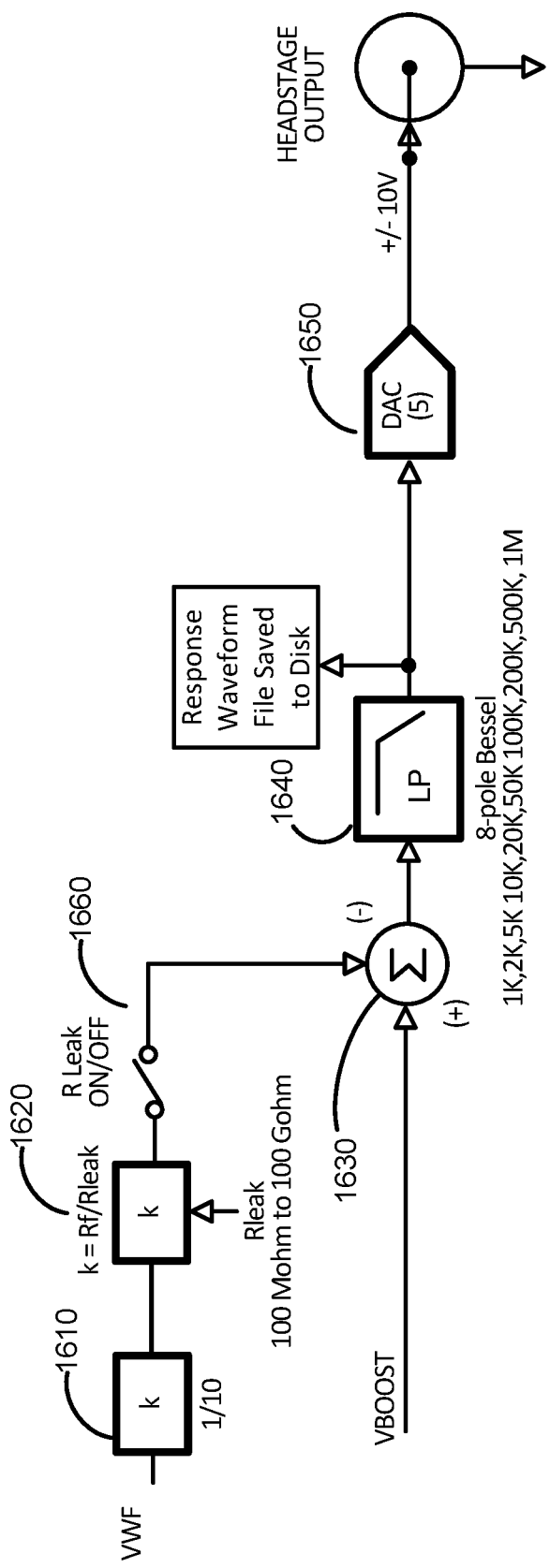
FIG. 17 illustrates an output conditioning and leak subtraction circuit according to an embodiment of the present invention.

FIG. 17 illustrates an output conditioning and leak subtraction circuit according to an embodiment of the present invention. This output conditioning and leak subtraction circuit may be utilized as the output signal conditioning and leak subtraction 570, or as output signal conditioning and leak subtraction circuits in other embodiments of the present invention.

In this example, the output of the waveform generator VWF may be gained or attenuated by gain stages 1610 and 1620 and summed with VBOOST at summing node 1630. The output of summing node 1630 may be filtered by low-pass filter 1640 and either saved to disk or provided as an analog signal by digital-to-analog converter 1650, or both. The leakage compensation path may be disabled by switch 1660. The low-pass filter 1640 may be a Bessel filter or other type of filter. The low-pass filter 1640 may have a variable bandwidth.

In the above examples, a voltage is forced onto a cell and a resulting current is measured. Again, this may be referred to as the voltage clamp configuration. In other test configurations consistent with embodiments of the present invention, a current is forced into a cell and the resulting voltage is measured. This may be referred to as the current clamp configuration. An example is shown in the following figure.

Figure 18:
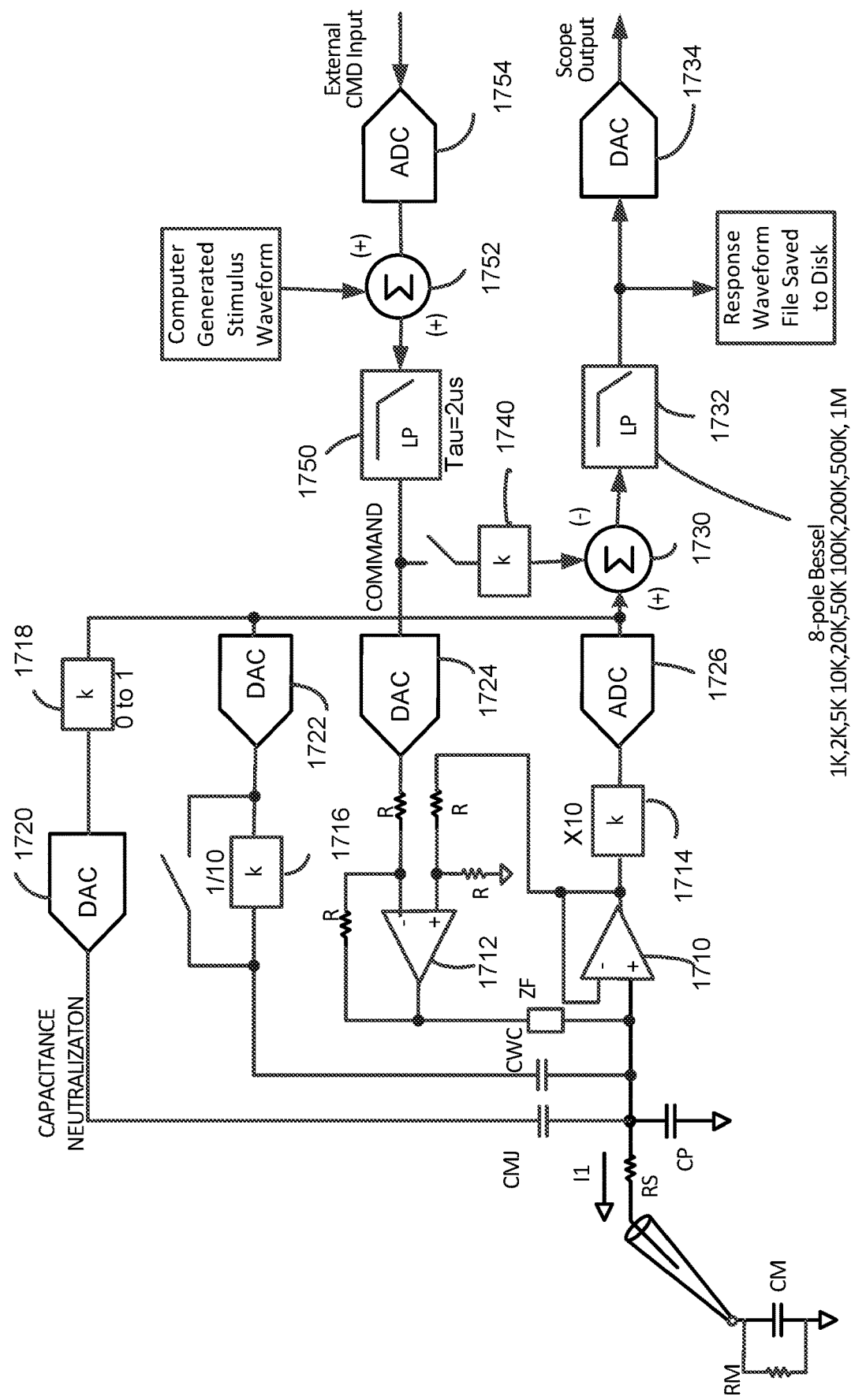
FIG. 18 illustrates a current clamp circuit according to an embodiment of the present invention.

FIG. 18 illustrates a current clamp circuit according to an embodiment of the present invention. The circuits shown here may be the same circuits as used in the above examples, but reconnected into this new configuration. For example, amplifier 1710 may be the same amplifier as amplifier 312. In a specific embodiment of the present invention, amplifier 312 may be internally reconfigured to have its inverting and non-inverting inputs reversed. Similarly, amplifier 1712 may be second amplifier 412 reconnected into this new configuration.

In this configuration, DAC 1724 may generate a current command, as compared to the voltage command in the above examples. DAC 1724 may generate a voltage that may be converted into a current by amplifier 1712 and its surrounding resistors. That is, a voltage across ZF may be generated such that a desired I1 is generated. This I1 is then forced into the output terminal and into the cell. A resulting voltage may then be measured.

Specifically, a command waveform may be received and converted by analog-to-digital converter 1754. Alternatively, a command waveform may be read from disk. The selected command waveform may be the output of summing node 1752 and may be filtered by low-pass filter 1750. The output of low-pass filter 1750 may be converted by digital-to-analog converter 1724, the command DAC, and provided to amplifier 1712. The command DAC 1724 may be the same DAC as DAC 326 in the above examples. In other embodiments of the present invention, DAC 1724 and DAC 326 may be different DACs. This may aid in allowing a rapid change over from operating in the voltage clamp mode shown above to the current clamp mode shown here.

A voltage may be generated across ZF, which may be the same ZF around amplifier 312 but reconnected. The forced voltage across ZF may generate a current that may be forced into the summing node and into the cell as current I1. The resulting voltage may be buffered by amplifier 1710, gained by gain stage 1714, and converted by analog-to-digital converter 1726 before being filtered by low-pass filter 1732. Low-pass filter 1732 may be the same as low-pass filter 1640 in the above example. The output of low-pass filter 1732 may then be stored and converted to an analog voltage, which may be observed using an oscilloscope.

In the earlier configuration where a voltage is forced onto a cell and a resulting current is measured—the voltage clamp configuration—capacitor CWC may be used to cancel the whole-cell capacitance of the sample. In this current clamp configuration, it may be desirable to measure the whole-cell capacitance of the cell, so such a cancellation may not be desired. But it may not be feasible to simply disconnect CWC from the circuit. A switch, relay, or microelectronic mechanical (MEM) switch may be used, but errors caused by the introduced capacitance, given the small value of CWC, may make the use of such a component undesirable.

Accordingly, embodiments of the present invention may provide a signal at the output of digital-to-analog converter 1722 to the CWC capacitor such that a net or differential voltage across CWC does not change. When the voltage across CWC does not change in the current clamp mode, no current flows through CWC. In this way, the CWC capacitance can be virtually disconnected. Specifically, the voltage at the output terminal may be received by amplifier 1710 and gained by analog gain stage 1714. This may be converted to a digital signal by analog-to-digital converter 1726. This may then be reconverted to an analog signal by digital-to-analog converter 1722, and attenuated by analog gain stage 1716. This may generate a voltage at a first terminal of the capacitor CWC that nearly replicates the signal at the second terminal of CWC, which is connected to the output terminal and the non-inverting input of amplifier 1710. In this way, the voltage across the capacitor CWC does not change (that is, it has a zero AC voltage), and CWC does not provide an input current into the output terminal. In other embodiments of the present invention, analog gain stage 1716 may be replaced by a digital gain stage at the input of digital-to-analog converter 1722.

The pipette capacitance CP may be compensated for using a technique referred to as capacitance neutralization. That is, gain stage 1718 and DAC 1720 may be used to generate a negative capacitance that cancels or neutralizes CP. Specifically, the output signal from analog-to-digital converter 1726 may be gained by a value between 0 and 1 by gain stage 1718 and converted by DAC 1720. DAC 1720 may then provide an analog voltage to capacitance CMJ. The step in voltage across the capacitor CMJ again generates a spike of current into the summing node. This spike of current (again, a spike here is a fast edge of current that exponentially decays) may compensate for the slowing down or roll off in current into the cell caused by the pipette capacitance CP. DACs 1722 and 1720 may be the same DACs as DACs 322 and 320 after reconnection into this new configuration.

The series resistance RS may generate a voltage proportional to the input current that is added to the actual output voltage. Accordingly, an embodiment of the present invention may subtract a portion of the input command from the output voltage to compensate. Specifically, gain stage 1740 may generate a portion of the voltage used to generate the current to be input to the cell and RS. This voltage is subtracted from the output of analog-to-digital converter 1726 to compensate for the increase in voltage at the output of analog-to-digital converter 1726 due to the presence of RS.

In this embodiment of the present invention, a feedback loop is formed through gain stage 1718, DAC 1720, amplifier 1710, gain stage 1714, and analog-to-digital converter 1726. As such, this loop may oscillate. Accordingly, embodiments of the present invention may adjust the frequency response of one or more of these loop components to avoid an oscillatory condition.

By utilizing many of the same circuits in this current clamp configuration and the above voltage clamp configuration, test circuits provided by embodiments of the present invention may alternate between the two modes in a rapid manner. This may allow a technique referred to as discontinuous voltage clamping. This may have the effect of removing the series resistance RS from the measurements and may result in a more reliable system.

In other embodiments the present invention, it may be desirable to provide a conductance to a cell. This may be used to mimic current and voltage conditions that may be applied to a cell from a neighboring cell, or for other reasons. In this way, an embodiment of the present invention may mimic signals provided by an adjoining cell and measure the results. The circuitry shown above for the voltage clamp circuit and the current clamp circuit may be reconfigured into a conductance clamp circuit, better known as dynamic clamp circuit. Specifically, the amplifiers, DACs, and filters, gain stages, and other circuits from above may be reused with additional circuitry to generate a time-varying command signal. Such a circuit is shown in the following figure.

Figure 19:
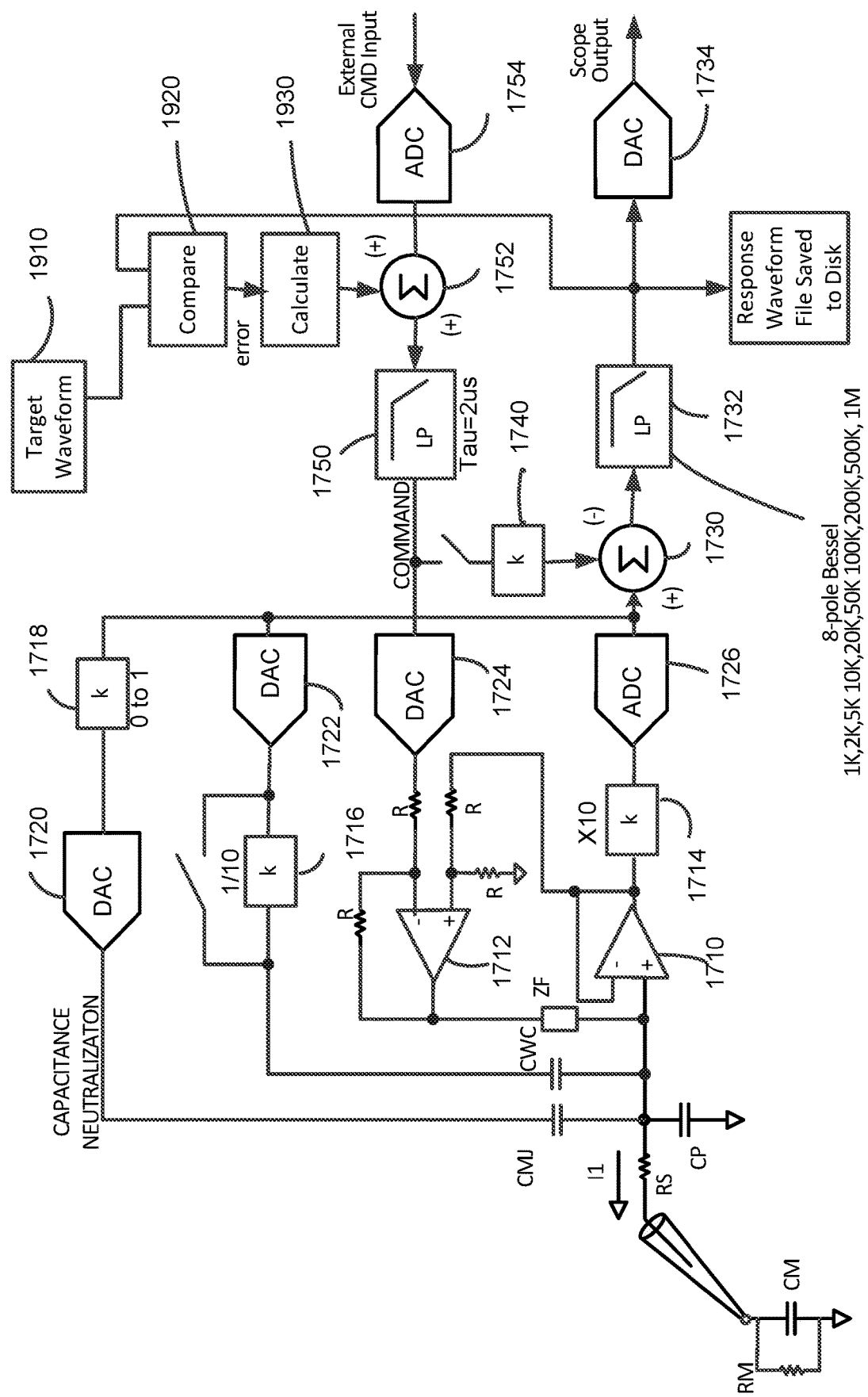
FIG. 19 illustrates a dynamic clamp circuit according to an embodiment of the present invention.

FIG. 19 illustrates a dynamic clamp circuit according to an embodiment of the present invention. As before, a digital command signal may be provided to DAC 1724. DAC 1724 may drive amplifier 1712. Amplifier 1712 may provide a voltage equal to, or proportional to, the command voltage across the impedance ZF to generate a command current I1 into the sample. The resulting voltage may be buffered by amplifier 1710, gained by a gain stage 1714, and converted to a digital signal by analog-to-digital converter 1726. The output of analog-to-digital converter 1726 may be filtered by low-pass filter 1732 and the results may be recorded or observed as before.

The amplitude of the command current, which is the amplitude of the command voltage provided to DAC 1724 divided by impedance ZF, and the resulting voltage at the output of low-pass filter 1732 may be used to determine a measured conductance. A value of the target conductance at a next point in time may be read from memory 1910. The measured conductance may be compared to the target conductance by compare block 1920 to generate a comparison or error signal. The error signal may be used to generate a new amplitude for the command signal by calculate block 1930.

Figure 20:
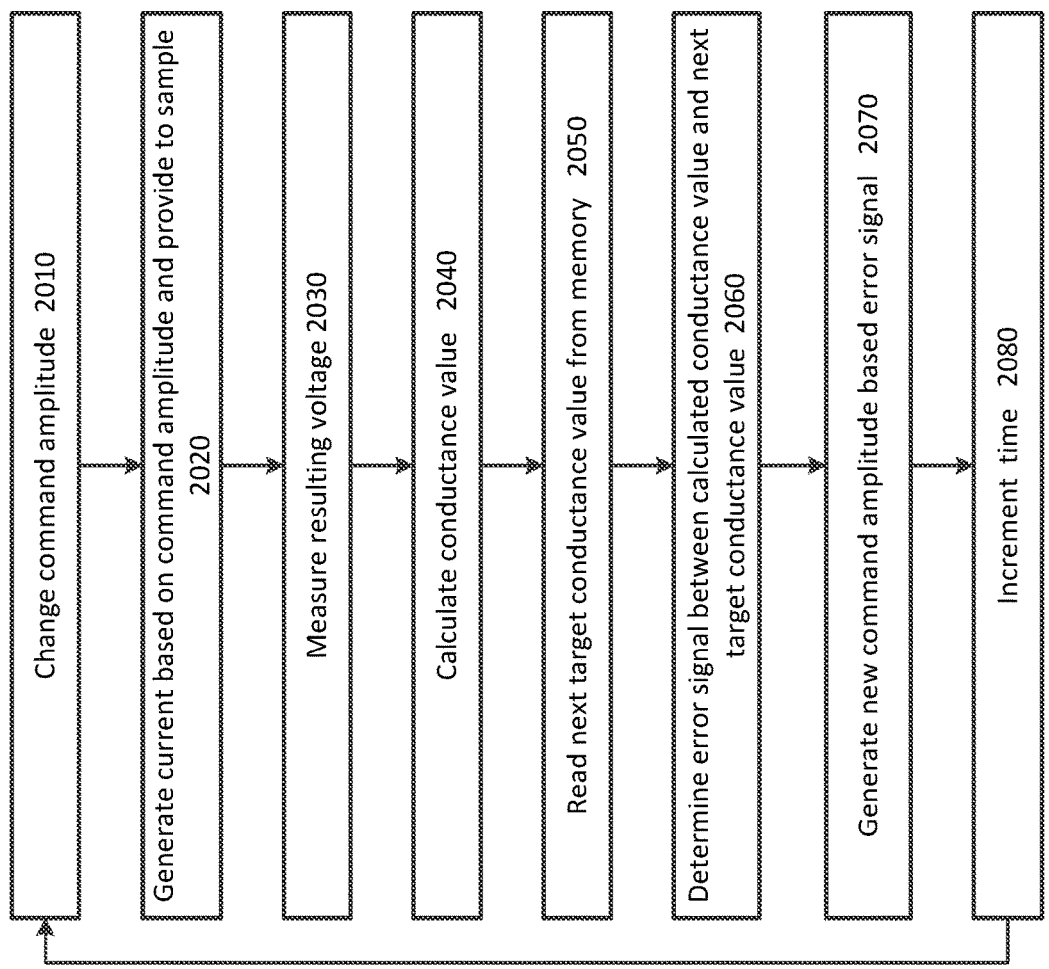
FIG. 20 is a flowchart showing the operation of a dynamic clamp circuit according to an embodiment of the present invention.

FIG. 20 is a flowchart illustrating the operation of a dynamic clamp circuit according to an embodiment of the present invention. In act 2010, an amplitude of a command signal is changed. The first time through this loop, feedback conditions may not have been established. Accordingly, an initial command amplitude may be read from memory, determined based on past results, or determined in other ways. From this command signal amplitude, a current into the sample may be generated in act 2020. A resulting voltage may be measured in act 2030. From this, a measured value may be calculated in act 2040.

A target conductance value may be read from memory in act 2050. The target conductance value may be for a next point in time. The measured conductance value may be compared to this target conductance in act 2060. From the difference in these values, an error signal may be determined. A new command amplitude may be determined based on the error signal in act 2070. Time may be incremented in act 2080. The command amplitude may be changed as the loop returns to act 2010.

In these and other embodiments of the present invention, a new command amplitude may be determined based on the error signal in different ways. In one embodiment of the present invention, the change in amplitude of the command signal is the change in amplitude needed to change the measured conductance an amount equal to the error signal. In one embodiment of the present invention, this may be determined by changing the command signal a number of steps that correlates to the error signal.

The correlation may be determined by utilizing typical current-to-voltage relationships for a sample. That is, by knowing a typical current-to-voltage relationship for a sample, it may be determined how much of a change in current into the cell is needed to achieve a result of a desired change in conductance. For a given error signal in the conductance, the needed change in sample current can be approximated and the command signal can be changed accordingly.

In another embodiment of the present invention, the clock rate of the signal generating the command signal may be fast enough that the change in command signal can track the change in target conductance by incrementing up or down once every time period. At each time period, which may be one or more FPGA clock cycles, the command signal may be incremented when the conductance is to be increased and decremented when the conductance is to be decreased. That is, the command signal may be incremented by one bit when the error signal is positive and decremented by one bit when the error signal is negative.

In another embodiment of the present invention, if the magnitude of the error signal is greater than a first threshold, then the command signal may be incremented up or down two bits as needed. This may be extended to any number of thresholds and any number of bits.

In these and other embodiments of the present invention, the signals in a measurement system may be converted between analog and digital signals at various locations in different signal paths. For example in FIG. 3, a digital command signal may be provided by FPGA 330 to digital-to-analog converter 326. Digital-to-analog converter 326 may provide the analog command signal to amplifier 312. Instead of limiting the use of the analog command signal in this way, it may also be used in generating a whole-cell compensation signal. That is, instead of digitally adding the digital command signal to a filtered version of the waveform generator output as shown above, the analog command signal may be added to an analog version of the filtered version of the waveform generator output. An example is shown in the following figure.

Figure 21:
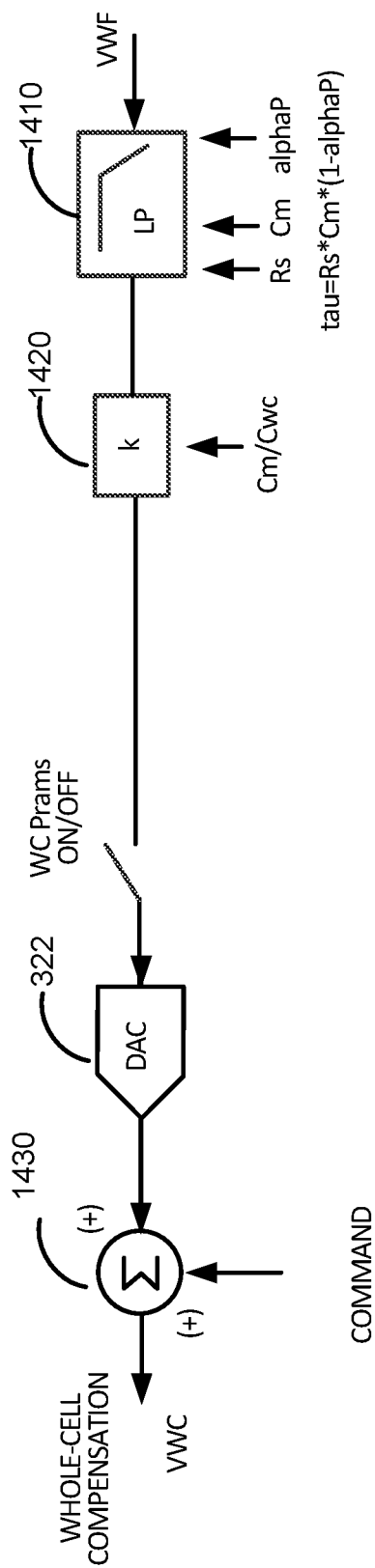
FIG. 21 illustrates another whole-cell compensation circuit according to an embodiment of the present invention.

FIG. 21 illustrates another whole-cell compensation circuit according to an embodiment of the present invention. A step or other function that is used to provide the command signal may be received by this whole-cell compensation path. This signal may be low-pass filtered, which essentially integrates the step or other function. The resulting voltage may be gained by a ratio of the whole-cell capacitance to a coupling capacitor used to couple an output voltage of the whole-cell compensation path. This signal may be converted to an analog signal. The analog command signal may then be added to this signal to generate an output voltage. The whole-cell compensation output voltage may then be applied through a capacitor, which essentially takes the derivative of the output voltage and provides a current to the input. This current may then at least approximately cancel the current drawn by the cell capacitance.

Specifically, the waveform generator output signal VWF may be received at low-pass filter 1410. The output of the low-pass filter 1410 may be received by gain stage 1420. This output may be provided by FPGA 330 in FIG. 3 to digital-to-analog converter 322. The output may be converted to an analog signal by digital-to-analog converter 322 before being added to the analog COMMAND signal (provided by digital-to-analog converter 326 in FIG. 3) at summing node 1430 to generate whole-cell compensation signal, the waveform VWC, which may be provided to capacitor CWCC, as shown above.

Unfortunately, this whole-cell capacitor CWCC may inject noise into the input of the headstage 510 (shown in FIG. 5.) Accordingly, these and other embodiments of the present invention may digitally subtract the whole-cell compensation signal from the headstage output signal before providing the resulting signal to the series resistance correction and prediction circuit. This may allow the removal of the CWCC capacitor (shown in FIG. 5) and its attendant noise. An example is shown in the following figure.

Figure 22:
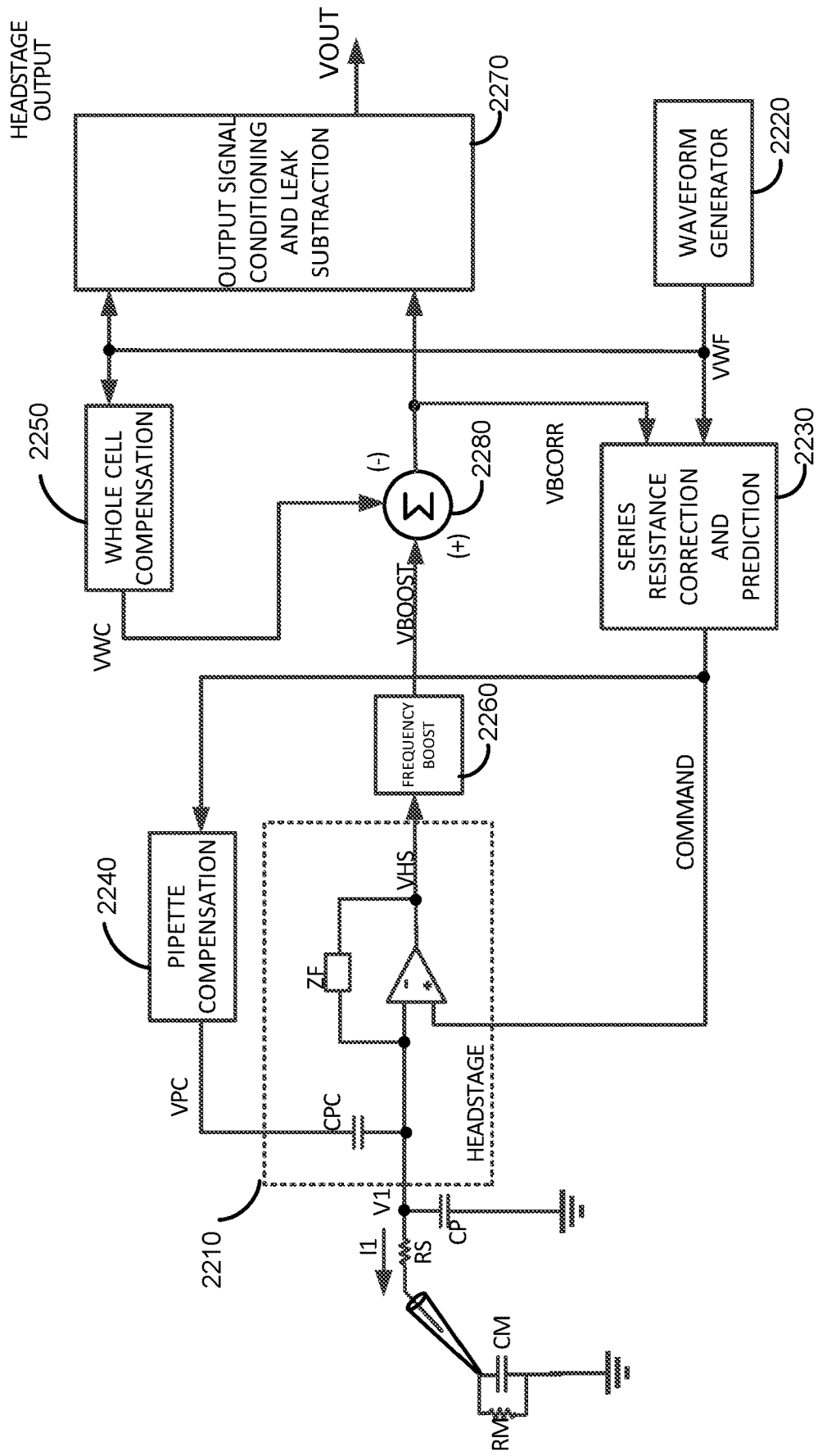
FIG. 22 illustrates another system diagram for a measurement system according to an embodiment of the present invention.

FIG. 22 illustrates another system diagram for a measurement system according to an embodiment of the present invention. In this example, pipette compensation 2240 and whole-cell compensation 2250 are shown as separate circuits. A frequency boost 2260 and output signal conditioning and leak subtraction 2270 are also included. In this example, an amplifier, such as amplifier 110 (shown in FIG. 1), may be implemented using headstage 2210, waveform generator 2220, series resistance correction and prediction 2230, pipette compensation 2240, whole-cell compensation 2250, frequency boost 2260, output signal conditioning and leak subtraction 2270, and summing node 2280. In one embodiment of the present invention, these circuits, except for headstage 2210, may be implemented using digital circuitry, such as FPGA 330 or 2330 (shown in FIG. 23.) Various data converters may be included at the interface of the FPGA and may be included in or separate from the FPGA. Waveform generator 2220, series resistance correction and prediction 2230, pipette compensation 2240, whole-cell compensation 2250, frequency boost 2260, output signal conditioning and leak subtraction 2270, summing node 2280, and the other digital circuits shown here may be implemented on an FPGA, such as FPGA 2330 or FPGA 330, as synchronous digital hardware circuits. For example, summing node 2280, as with the other summing nodes shown herein, may be implemented as an adder or other circuit.

As before, waveform generator 2220 may generate a step or other function VWF. The waveform VWF may be received by series resistance correction and prediction 2230. Series resistance correction and prediction 2230 may generate a COMMAND signal, which may be received by headstage 2210. Headstage 2210 may receive the COMMAND signal and generate a voltage V1. Voltage V1 may be applied to a cell, with a resulting current I1. Current I1 may flow through feedback impedance ZF, thereby generating output voltage VHS. The output signal VHS may be amplified by frequency boost 2260 to generate the signal VBOOST. The VBOOST signal may be received by the summing node 2280.

The COMMAND signal may be used by pipette compensation 2240 to provide a voltage VPC. The voltage VPC may generate a current through capacitor CPC that may at least reduce or cancel a current in pipette capacitance CP. The step or other function VWF may be provided to whole-cell compensation 2250 from waveform generator 2220. Whole-cell compensation 2250 may generate a voltage VWC, which may be received by summing node 2280. The voltage VWC may be subtracted from the boosted version of the headstage output, VBOOST, to generate a corrected output signal VBCORR. This VBCORR output may be provided to the series resistance correction and prediction 2230. Specifically, the VBCORR signal may be received at the input labeled VBOOST in the example series resistance correction and prediction shown in FIG. 14. In this way, the output of the series resistance correction and prediction 2230 is modified to at least reduce or compensate for current generated by capacitance CM at the cell membrane. This may eliminate the need to inject a current through capacitor CWCC as shown in FIG. 5, thereby reducing the noise of the amplifier.

Output signal conditioning and leak subtraction 2270 may receive the corrected output signal VBCORR from summing node 2280 and may filter VBCORR and provide it as an output VOUT. Output signal conditioning and leak subtraction 2270 may also receive the output of waveform generator 2220 and may compensate for the leakage path formed by the combination of the series resistance RS and cell membrane resistance RM.

Figure 23:
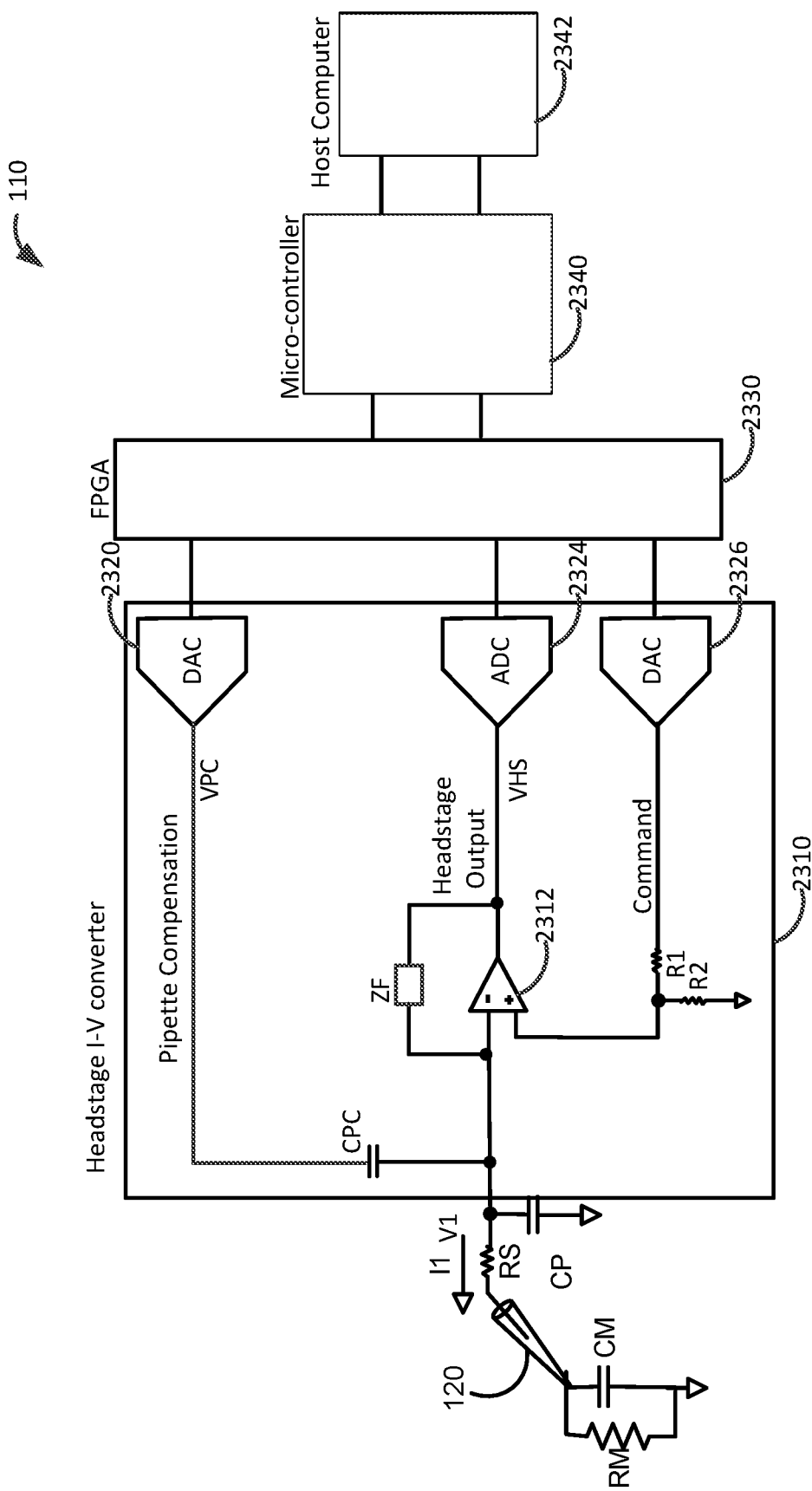
FIG. 23 illustrates another system diagram of a measurement system according to an embodiment of the present invention.

FIG. 23 illustrates another system diagram of a measurement system according to an embodiment of the present invention. This measurement system may include a headstage 2310, FPGA 2330, microcontroller 2340, and a host computer 2342. In this example, an amplifier, such as amplifier 110 (shown in FIG. 1), may be implemented by headstage 2310 and FPGA 2330.

In this system, FPGA 2330 may provide a digital function to digital-to-analog converter 2326. Digital-to-analog converter 2326 may convert the digital signal to an analog COMMAND signal. In this and other embodiments of the present invention, the digital function and the resulting COMMAND signal, may be a step, pulse, sine wave, ramp, saw-tooth, triangle wave, or other different or arbitrarily-shaped function. The analog COMMAND signal may be received at a non-inverting input of amplifier 2312. Amplifier 2312 may be configured as a trans-impedance amplifier. Amplifier 2312 may drive voltage V1 such that it is equal to the analog command signal. The voltage V1 may be applied to membrane or sample 140 via pipette 120. The resulting current I1 may pass through feedback impedance ZF, thereby generating voltage VHS. The voltage VHS may be converted to a digital signal by analog-to-digital converter 2324 and provided to the FPGA 2330. In these and other embodiments of the present invention, FPGA 2330, which may be the same, similar, or different from FPGA 330, may be use to implement the synchronous digital hardware circuits disclosed herein.

Again, the parasitic components of the cell may degrade the signal V1. Accordingly, FPGA 2330 may provide a V1 that is pre-compensated such that the actual V1 seen by the cell is a desired waveform. Also, the parasitic components in this measurement system may create currents. These currents may be compensated for by embodiments of the present invention. In this example, FPGA 2330 may provide a pipette compensation signal VPC via a digital-to-analog converter 2320 to capacitor CPC. The voltage applied at capacitor CPC relative to V1 may generate a current to compensate for a current generated by the pipette capacitance CP. Similarly, the FPGA 2330 may provide whole-cell compensation to compensate for a current generated by the membrane capacitance of sample 140. This whole-cell compensation may be generated in FPGA 2330 and used to modify the COMMAND signal in the manner shown in FIG. 22.

As before, FPGA 2330 may be controlled by microcontroller 2340. Microcontroller 2340 may be used to load configuration data into FPGA 2330 at start-up, reset, or other appropriate times. The microcontroller 2340 may also be used to pass gain settings, constants, or other variables or values to FPGA 2330.

The host computer 2342 may provide a user interface to the measurement system. In a specific example, a user may input a bandwidth for a filter into host computer 2342 using a graphical user interface. Microcontroller 2340 may fetch the bandwidth value from the host and calculate the needed filter constants. The filter constants may then be sent from the microcontroller 2340 to the FPGA 2330, which may then configure the filter.

In these examples, analog-to-digital and digital-to-analog converters may be used to convert signals between the headstage circuit and the one or more compensation and other circuits. These converters may be located close to the headstage to reduce noise coupling on the analog signal lines. In a specific example, the headstage 2310, analog-to-digital converter 2324, and digital-to-analog converters 2320 and 2326 are in a first box or on a first board that may be placed near the pipette 120 and sample 140 during operation, while the FPGA 2330 is in a second remote box or on a second remote board, where one or more cables convey the digital information between the two boxes.

Figure 24:
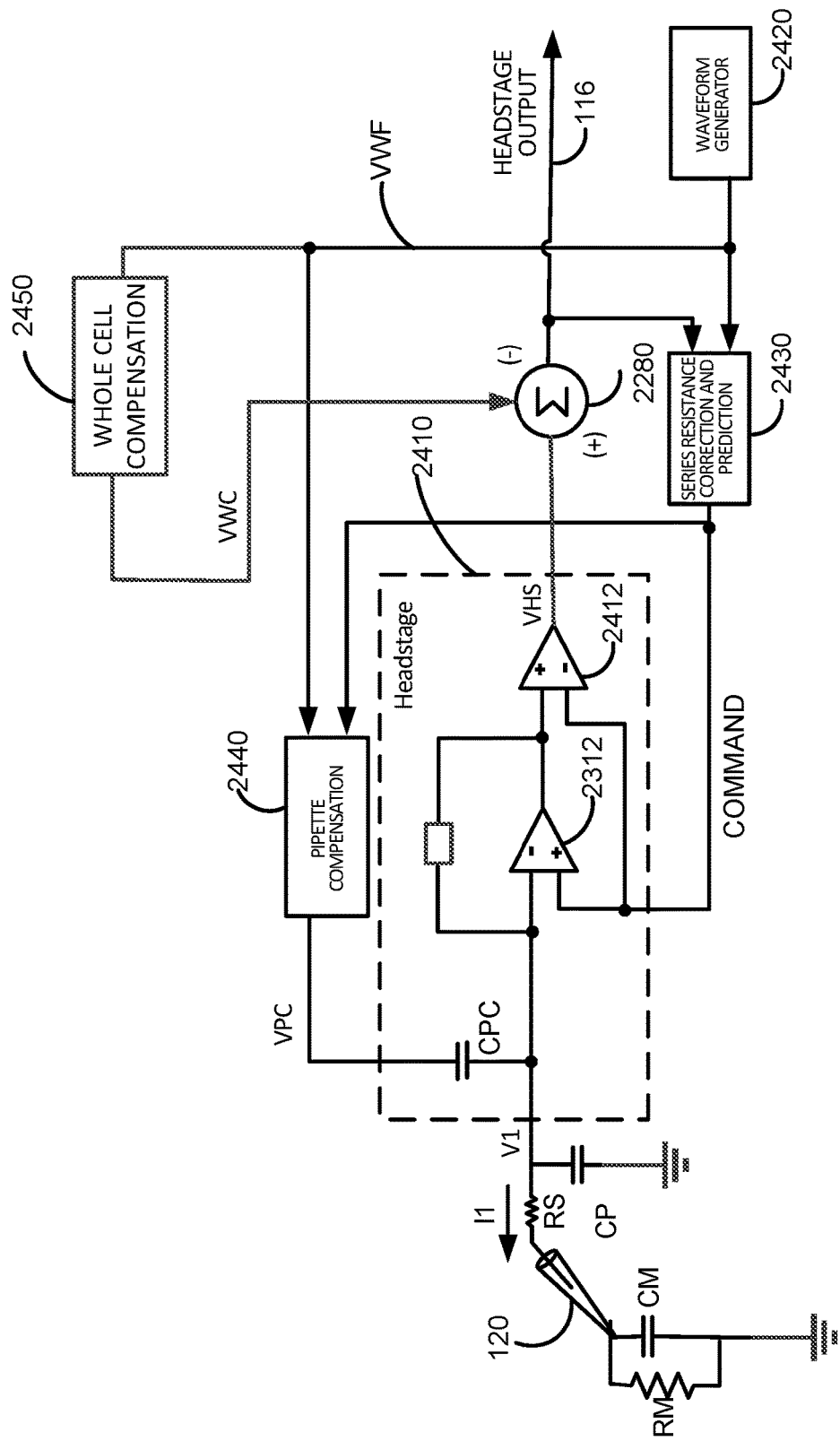
FIG. 24 illustrates another system diagram of a measurement system according to an embodiment of the present invention.

FIG. 24 illustrates another system diagram of a measurement system according to an embodiment of the present invention. In this example, an amplifier, such as amplifier 110 (shown in FIG. 1), may be implemented using headstage 2410, waveform generator 2420, series resistance correction and prediction 2430, and pipette compensation 2440 and whole-cell compensation 2450. In various embodiments of the present invention, waveform generator 2420, series resistance correction and prediction 2430, pipette compensation 2240, and whole-cell compensation 2450 may be implemented using an FPGA or other programmable circuitry, such as FPGA 2330. Waveform generator 2420, series resistance correction and prediction 2430, pipette compensation 2440 and whole-cell compensation 2450, and the other digital circuits shown here may be implemented on an FPGA, such as FPGA 2330 or FPGA 330, as synchronous digital hardware circuits.

The waveform generator 2420 may generate a step or other function VWF, which may then be modified to be applied to the cell membrane. Again, parasitic components may degrade the generated step or other function before it reaches the cell. Accordingly, a series resistance correction and prediction 2430 may adjust this step or other function VWF and generate a COMMAND signal, which it may provide to headstage 2410.

More specifically, the cell may see a capacitance CM in parallel with resistors RS and RM. Since the resistance RM of the membrane may be large, this parallel combination may be simplified to the capacitance CM and resistance RS. These components may effectively create a time constant at the cell membrane, which may have the effect of rolling off a leading edge of a step or other function applied to the cell. To compensate for this roll off, a boost or overshoot may be added to the waveform VWF generated by waveform generator 2420 by the series resistance correction and prediction 2430. The waveform VWF generated by waveform generator 2420 may also be received by whole-cell compensation 2450, which may generate a whole-cell compensation signal VWC. The whole-cell compensation signal VWC may be received by summing node 2280.

The COMMAND signal may be received by headstage 2410, which may in turn generate the input voltage to the cell, V1. The step waveform V1 may generate a current through the pipette capacitance CP. To compensate for the current through capacitance CP, pipette compensation may receive the COMMAND signal and the step function VWF from waveform generator 2420 and generate a voltage VPC at capacitor CPC. Similarly, the applied voltage at the cell may generate a current through capacitor CM. To compensate for the current in capacitor CM, whole-cell compensation 2450 may also provide the voltage VWC to summing node 2280. This signal may be subtracted from the headstage output VHS (or VBOOST as shown in FIG. 22) and provided to series resistance correction and prediction 2430 to reduce or cancel the effect of the current in the membrane capacitance CM. Specifically, the VBCORR signal may be received at the input labeled VBOOST in the example series resistance correction and prediction shown in FIG. 14.

In this specific example, a second amplifier 2412 in headstage 2410 may be used to subtract the COMMAND signal from the output of amplifier 2312, since the COMMAND signal would otherwise be added to the output signal VHS. In other embodiments of the present invention, this subtraction function may be implemented digitally, for example in FPGA 2330.

Figure 25:
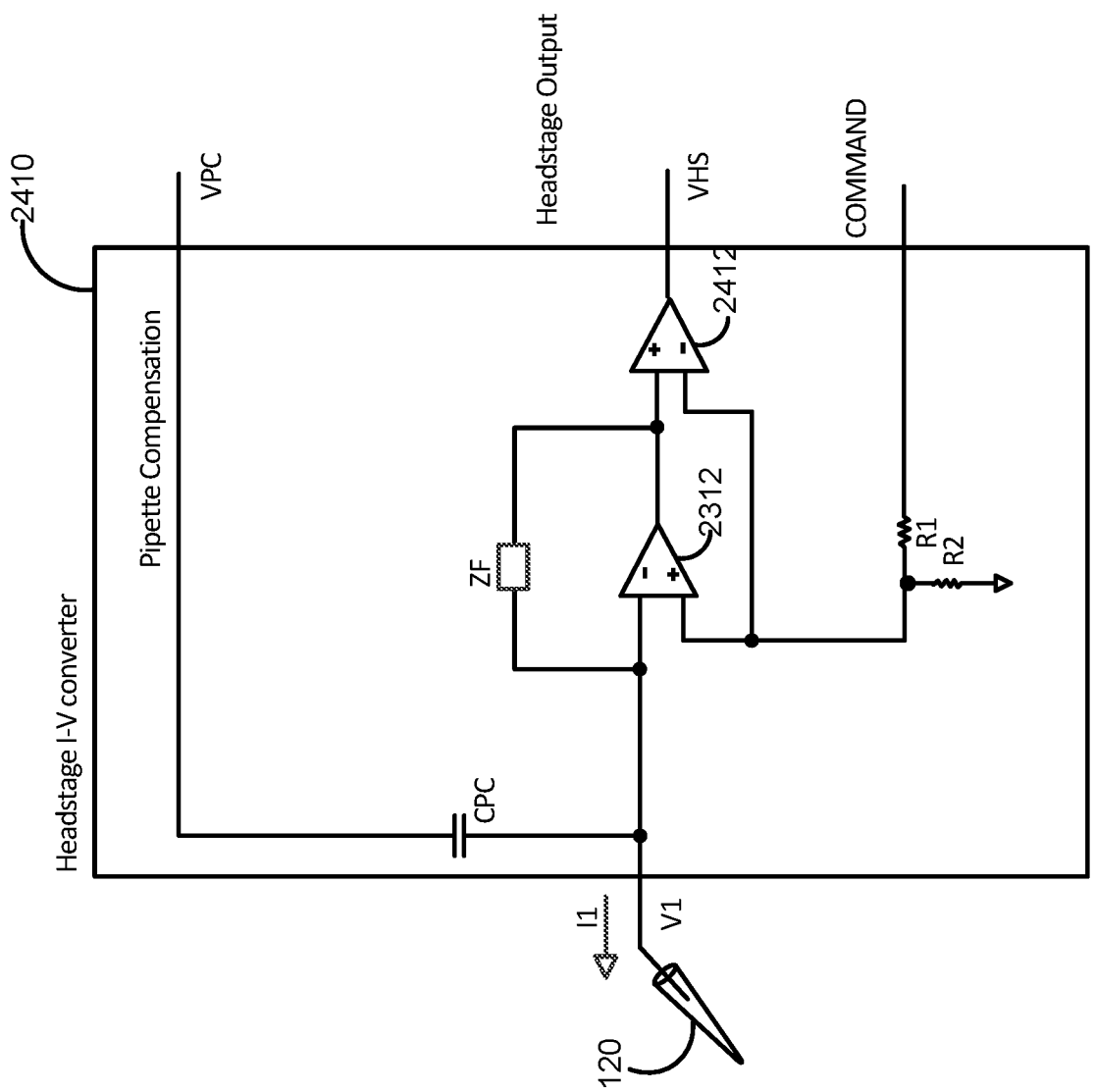
FIG. 25 illustrates another headstage according to an embodiment of the present invention

FIG. 25 illustrates another headstage according to an embodiment of the present invention. As before, headstage 2410 may receive a COMMAND signal. This COMMAND signal may be a step or other function with an overshoot, where the overshoot has been adjusted to compensate for an RC time constant at the cell sample. The COMMAND signal may be received at the non-inverting inputs of amplifier 2312. The amplifier 2312 may drive voltage V1 to track the COMMAND signal. V1 may be received by the cell and may generate a current I1. Current I1 may flow through feedback impedance ZF to create a signal at a non-inverting input of second amplifier 2412. Second amplifier 2412 may be configured to subtract the COMMAND signal from the resulting voltage and provide an output signal VHS.

A pipette compensation path may provide a voltage VPC to capacitor CPC, which may create a current to compensate for a current flowing in the pipette capacitance CP.

Figure 26:
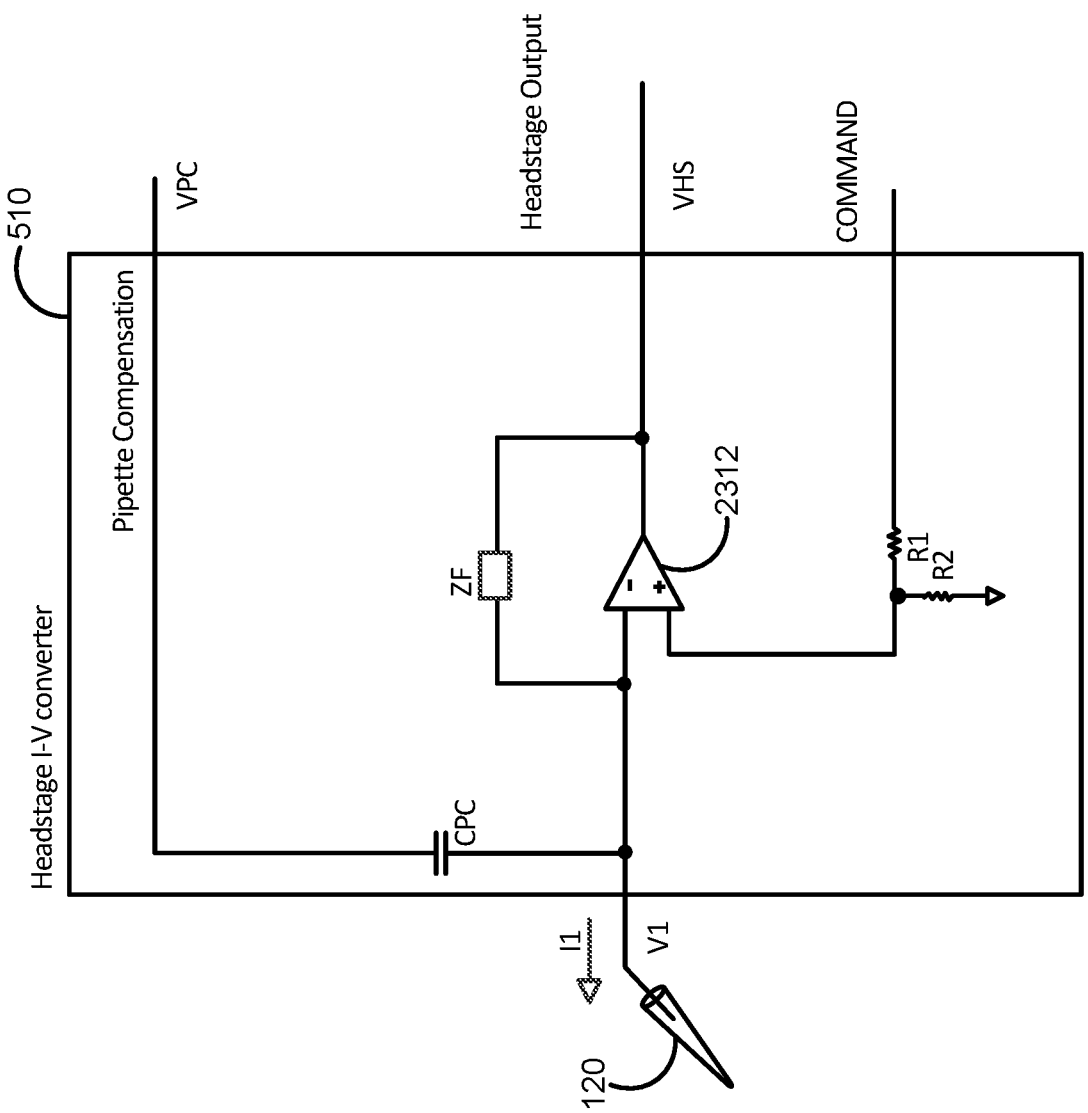
FIG. 26 illustrates another headstage according to an embodiment of the present invention.

FIG. 26 illustrates another headstage according to an embodiment of the present invention. In this example, the second amplifier 412 may be omitted, and the command signal may be digitally subtracted from the output signal VHS. An example of how this may be done is shown in the following figure.

Figure 27:
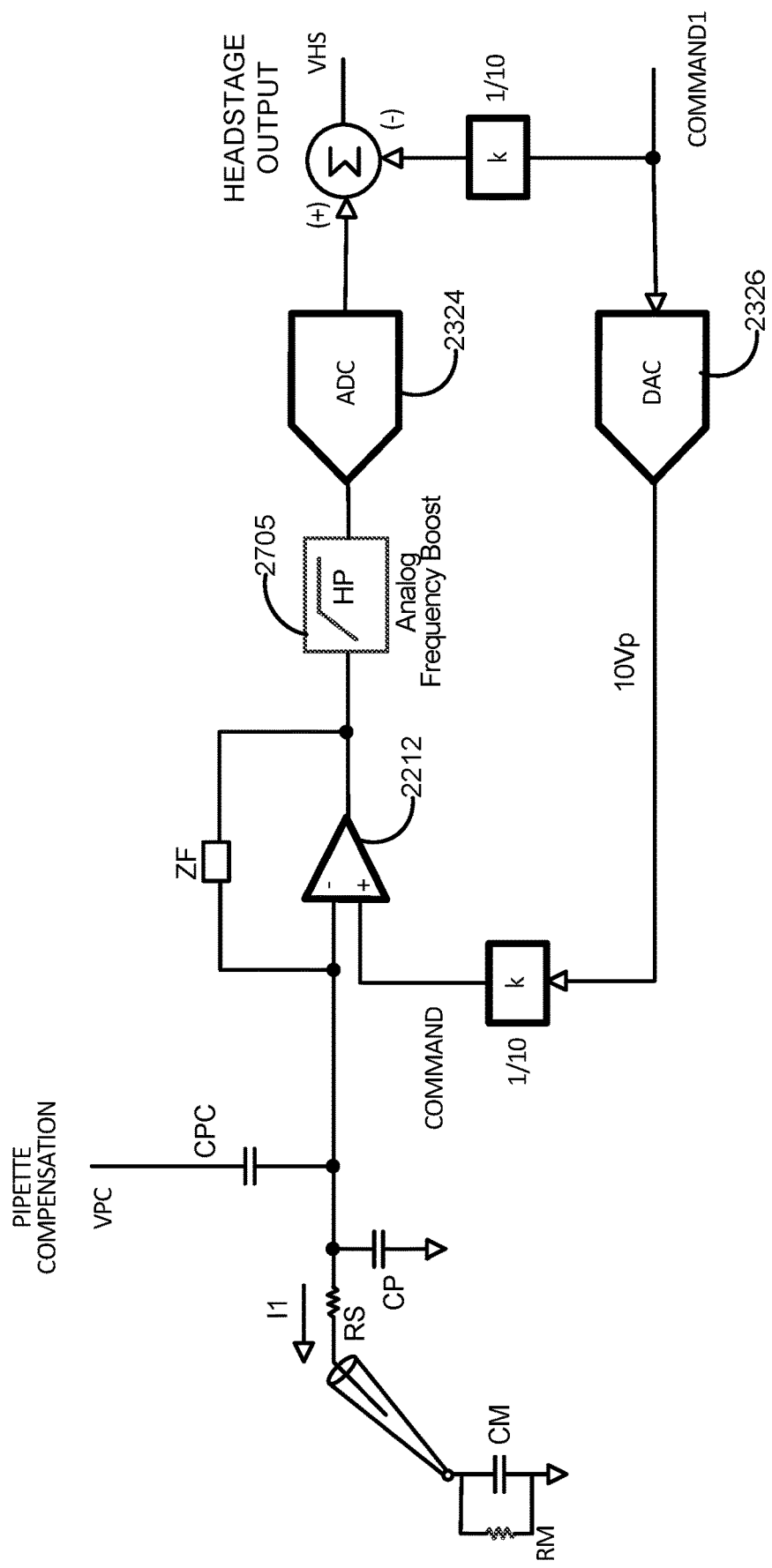
FIG. 27 illustrates another headstage according to an embodiment of the present invention.

FIG. 27 illustrates another headstage according to an embodiment of the present invention. In this example, the feedback component ZF may be resistive. As before, a digital command signal, referred to here as the COMMAND1 signal to avoid confusion with the analog COMMAND signal, may be received by digital-to-analog converter 2326. Digital-to-analog converter 2326 may provide an output that is attenuated by a factor "k," which provides the analog COMMAND signal to a non-inverting input of amplifier 2212. As before, amplifier 2212 may drive V1 to follow the command signal. This may in turn generate a current I1, which may flow across impedance ZF, which may be a resistance, generating a voltage at an input of analog frequency boost or high-pass filter 2705. An output of analog frequency boost or high-pass filter 2705 may be received at an input of analog-to-digital converter 2324. The command signal may be divided by a factor "k" and subtracted from the output of the analog-to-digital converter 2324 to generate an upper voltage VHS.

In this example, attenuation blocks may provide attenuation factor of 0.1. This may allow the use of a larger dynamic signal as the COMMAND1 signal. This may provide a benefit in that more of the dynamic range of digital-to-analog converter 2326 may be utilized and the quantization error of digital-to-analog converter 2326 may be reduced by a factor of 10.

As before, capacitor CPC may receive a voltage to compensate for currents in capacitance CP, respectively.

Figure 28:
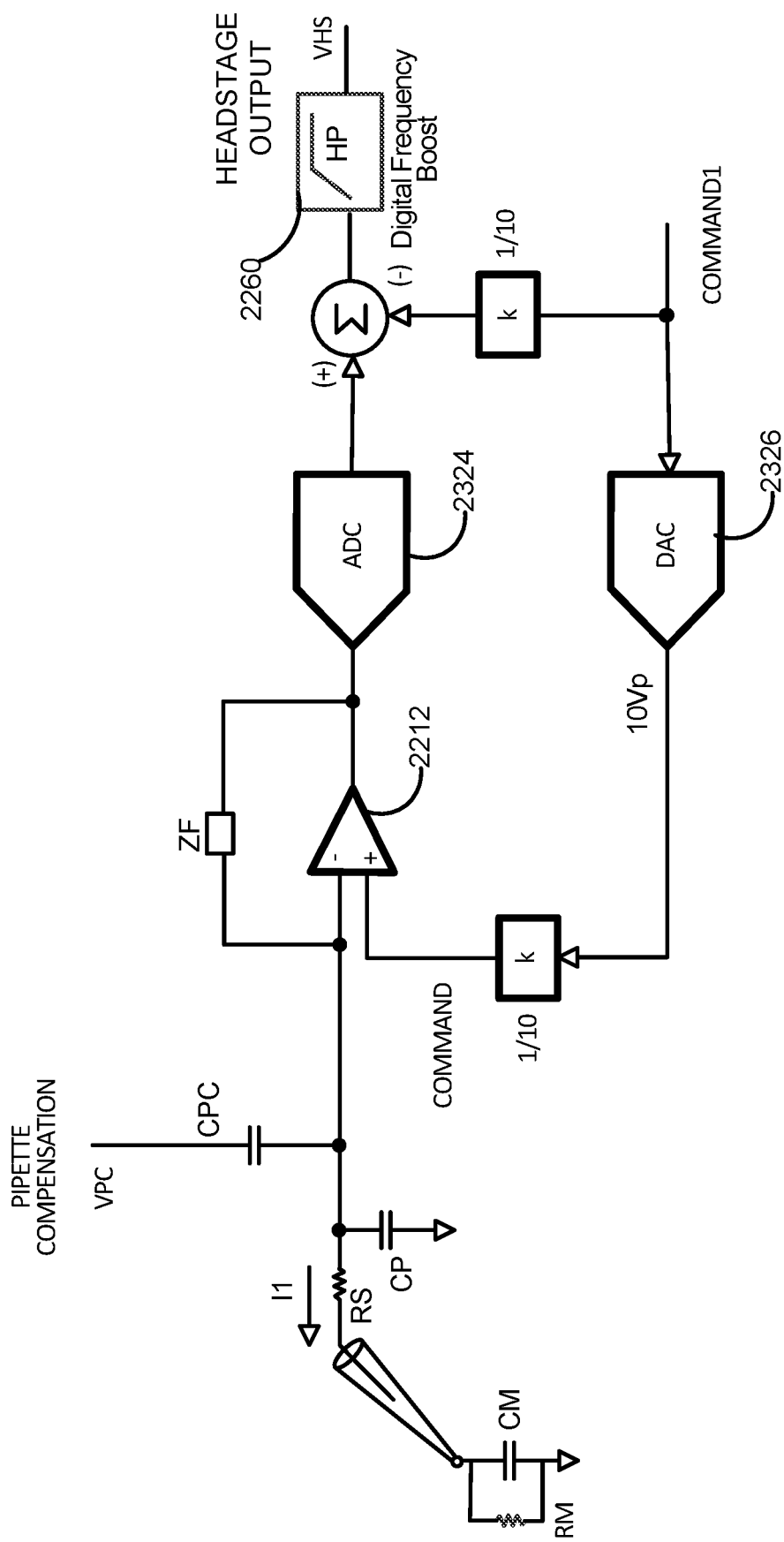
FIG. 28 illustrates another headstage according to an embodiment of the present invention.

FIG. 28 illustrates another headstage according to an embodiment of the present invention. In this example, feedback component ZF may be capacitive. Instead of passing the output of amplifier 2212 through analog frequency boost or high-pass filter 2705 (in FIG. 27), the output of amplifier 2212 may be converted to a digital signal by analog-to-digital converter 2324. The output of analog-to-digital converter 2324 may be summed with a gained portion of the COMMAND1 signal, where the gain may be an attenuation of approximately one-tenth. This attenuation may match the attenuation in the analog COMMAND path, making the attenuated COMMAND1 signal equal in amplitude, but in digital form, to the analog COMMAND signal applied to the inverting input of amplifier 2312. The summed value may then be boosted by digital frequency boost or high-pass filter 2260 before being provided as the output of the headstage.

Figure 29:
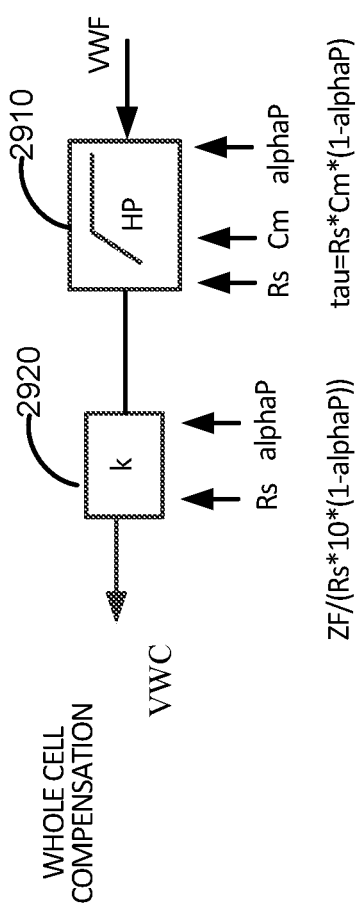
FIG. 29 illustrates another whole-cell compensation circuit according to an embodiment of the present invention.

FIG. 29 illustrates another whole-cell compensation circuit according to an embodiment of the present invention. A step or other function that is used to provide the command signal may be received by this whole-cell compensation path. This signal may be high-pass filtered, which essentially takes the derivative of the step or other function. The resulting voltage may then be gained and provided as an output that is subtracted from the headstage output to at least approximately cancel the current drawn by the cell capacitance.

Specifically, the waveform generator output signal VWF may be received at high-pass filter 2910. The output of the high-pass filter 2910 may be received by gain stage 2920. This whole-cell compensation signal VWC may be provided to a summing node, such as summing node 2280 in FIG. 22. The output of summing node 2280 may then be input to the series resistance correction and prediction 2230, as shown in FIG. 22.

Figure 30:
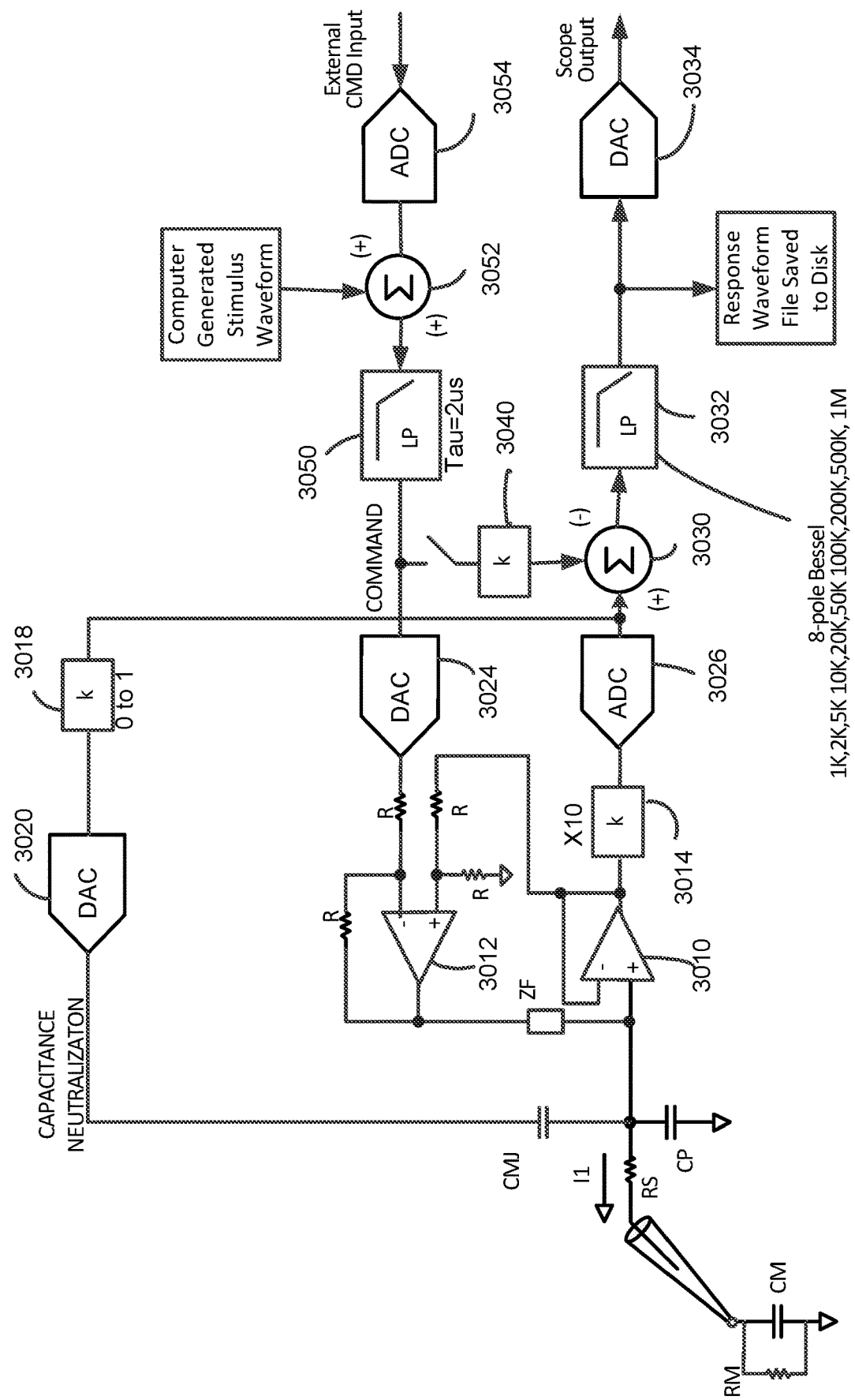
FIG. 30 illustrates a current clamp circuit according to an embodiment of the present invention.

FIG. 30 illustrates a current clamp circuit according to an embodiment of the present invention. The circuits shown here may be the same circuits as used in the above examples, but reconnected into this new configuration. For example, amplifier 3010 may be the same amplifier as amplifier 312 (shown in FIG. 3.) In a specific embodiment of the present invention, amplifier 312 may be internally reconfigured to have its inverting and non-inverting inputs reversed. Similarly, amplifier 3012 may be amplifier 312 reconnected into this new configuration.

In this configuration, DAC 3024 may generate a current command, as compared to the voltage command in the above examples. DAC 3024 may generate a voltage that may be converted into a current by amplifier 3012 and its surrounding resistors. That is, a voltage across ZF may be generated such that a desired I1 is generated. This I1 is then forced into the output terminal and into the cell. A resulting voltage may then be measured.

Specifically, a command waveform may be received and converted by analog-to-digital converter 3054. Alternatively, a command waveform may be read from disk. The selected command waveform may be the output of summing node 3052 and may be filtered by low-pass filter 3050. The output of low-pass filter 3050 may be converted by digital-to-analog converter 3024, the command DAC, and provided to amplifier 3012. The command DAC 3024 may be the same DAC as DAC 326 in the above examples. In other embodiments of the present invention, DAC 3024 and DAC 326 may be different DACs. This may aid in allowing a rapid change over from operating in the voltage clamp mode shown above to the current clamp mode shown here.

A voltage may be generated across ZF, which may be the same ZF around amplifier 312 but reconnected. The forced voltage across ZF may generate a current that may be forced into the summing node and into the cell as current I1. The resulting voltage may be buffered by amplifier 3010, gained by gain stage 3014, and converted by analog-to-digital converter 3026 before being filtered by low-pass filter 3032. Low-pass filter 3032 may be the same as low-pass filter 1640 in the above example. The output of low-pass filter 3032 may then be stored and converted to an analog voltage, which may be observed using an oscilloscope.

The pipette capacitance CP may be compensated for using a technique referred to as capacitance neutralization. That is, gain stage 3018 and DAC 3020 may be used to generate a negative capacitance that cancels or neutralizes CP. Specifically, the output signal from analog-to-digital converter 3026 may be gained by a value between 0 and 1 by gain stage 3018 and converted by DAC 3020. DAC 3020 may then provide an analog voltage to capacitance CMJ. The step in voltage across the capacitor CMJ again generates a spike of current into the summing node. This spike of current (again, a spike here is a fast edge of current that exponentially decays) may compensate for the slowing down or roll off in current into the cell caused by the pipette capacitance CP. DAC 3020 may be the same DAC as DAC 320 (shown in FIG. 3) after reconnection into this new configuration.

The series resistance RS may generate a voltage proportional to the input current that is added to the actual output voltage. Accordingly, an embodiment of the present invention may subtract a portion of the input command from the output voltage to compensate. Specifically, gain stage 3040 may generate a portion of the voltage used to generate the current to be input to the cell and RS. This voltage is subtracted from the output of analog-to-digital converter 3026 to compensate for the increase in voltage at the output of analog-to-digital converter 3026 due to the presence of RS.

In this embodiment of the present invention, a feedback loop is formed through gain stage 3018, DAC 3020, amplifier 3010, gain stage 3014, and analog-to-digital converter 3026. As such, this loop may oscillate. Accordingly, embodiments of the present invention may adjust the frequency response of one or more of these loop components to avoid an oscillatory condition.

By utilizing many of the same circuits in this current clamp configuration and the above voltage clamp configuration, test circuits provided by embodiments of the present invention may alternate between the two modes in a rapid manner. This may allow a technique referred to as discontinuous voltage clamping. This may have the effect of removing the series resistance RS from the measurements and may result in a more reliable system.

In other embodiments of the present invention, it may be desirable to provide a conductance to a cell. This may be used to mimic current and voltage conditions that may be applied to a cell from a neighboring cell, or for other reasons. In this way, an embodiment of the present invention may mimic signals provided by an adjoining cell and measure the results. The circuitry shown above for the voltage clamp circuit and the current clamp circuit may be reconfigured into a conductance clamp circuit, better known as dynamic clamp circuit. Specifically, the amplifiers, DACs, and filters, gain stages, and other circuits from above may be reused with additional circuitry to generate a time-varying command signal. Such a circuit is shown in the following figure.

Figure 31:
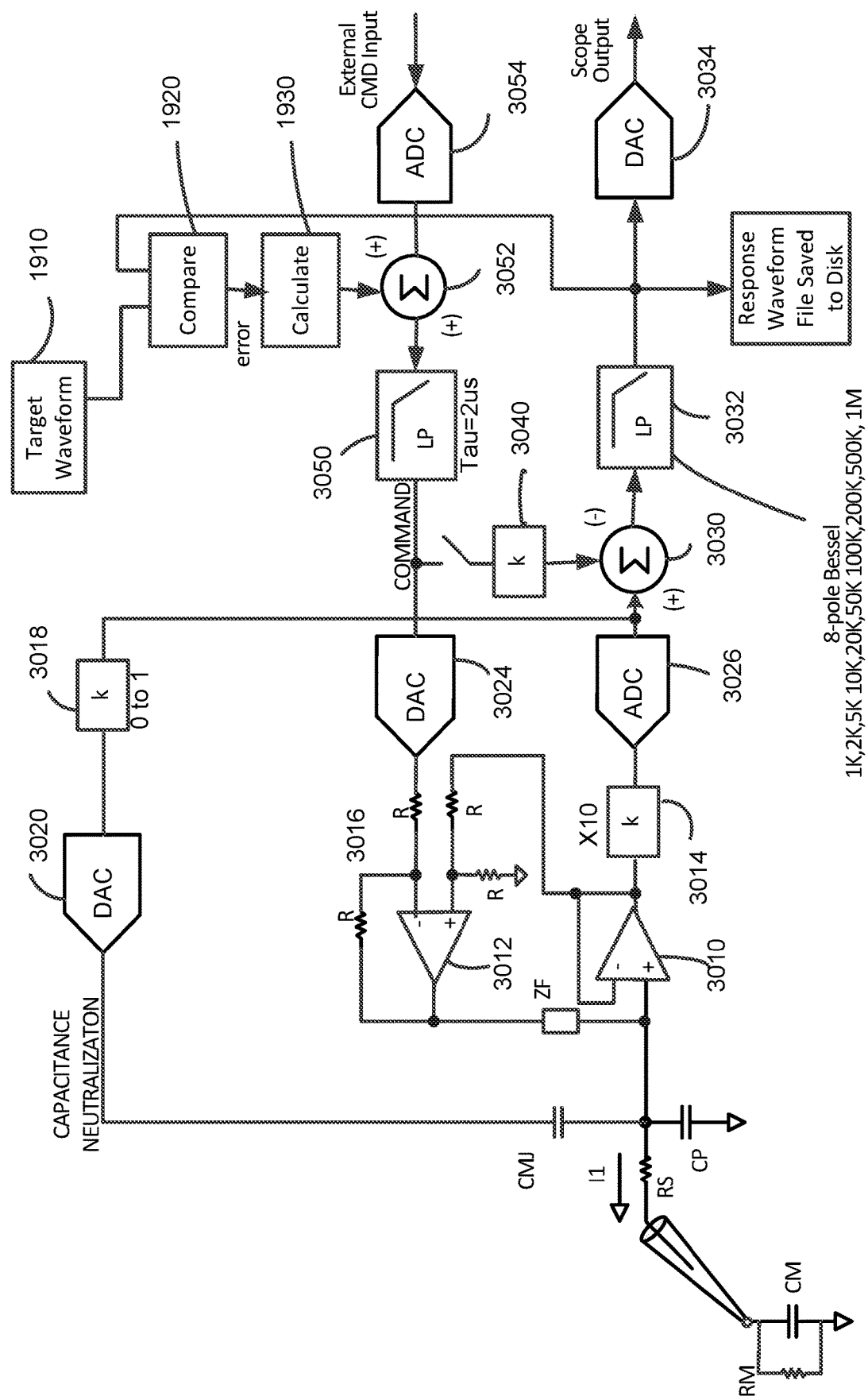
FIG. 31 illustrates a dynamic clamp circuit according to an embodiment of the present invention.

FIG. 31 illustrates a dynamic clamp circuit according to an embodiment of the present invention. As before, a digital command signal may be provided to DAC 3024. DAC 3024 may drive amplifier 3012. Amplifier 3012 may provide a voltage equal to, or proportional to, the command voltage across the impedance ZF to generate a command current I1 into the sample. The resulting voltage may be buffered by amplifier 3010, gained by gain stage 3014, and converted to a digital signal by analog-to-digital converter 3026. The output of analog-to-digital converter 3026 may be filtered by low-pass filter 3032 and the results may be recorded or observed as before.

The amplitude of the command current, which is the amplitude of the command voltage provided to DAC 3024 divided by impedance ZF, and the resulting voltage at the output of low-pass filter 3032 may be used to determine a measured conductance. A value of the target conductance at a next point in time may be read from memory 1910. The measured conductance may be compared to the target conductance by compare block 1920 to generate a comparison or error signal. The error signal may be used to generate a new amplitude for the command signal by calculate block 1930.

The above description of embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated. Thus, it will be appreciated that the invention is intended to cover all modifications and equivalents within the scope of the following claims.

What is claimed is:

1. An electronic device comprising:
a memory to store information for a digital waveform;
a digital waveform generator to receive the information and use the information to generate the digital waveform, wherein the digital waveform generator is a synchronous digital hardware circuit;
a series resistance compensation circuit to receive the digital waveform from the digital waveform generator and to provide a digital command signal, wherein the series resistance compensation circuit is a synchronous digital hardware circuit;
a first digital-to-analog converter to convert the digital command signal from the series resistance compensation circuit to an analog command signal;
a pipette compensation circuit to receive the digital command signal from the series resistance compensation circuit and to provide a digital pipette compensation signal, wherein the pipette compensation circuit comprises a synchronous digital hardware circuit;
a second digital-to-analog converter to convert the digital pipette compensation signal from the pipette compensation circuit to an analog pipette compensation signal;
a whole-cell compensation circuit to receive the digital waveform from the digital waveform generator and to provide a whole-cell compensation signal to a first circuit; and
a first analog circuit to receive the analog command signal and the analog pipette compensation signal, and to provide an analog headstage output signal to a first analog-to-digital converter, wherein the first analog-to-digital converter generates a digital headstage output signal,
wherein the first circuit receives the digital headstage output signal and subtracts the whole-cell compensation signal from the digital headstage output signal to generate a corrected digital headstage output signal,
wherein the series resistance compensation circuit further receives the corrected digital headstage output signal from the first circuit, and
wherein the digital waveform generator, the series resistance compensation circuit, and the pipette compensation circuit, and the whole-cell compensation circuit are implemented on a field-programmable gate array.

2. The electronic device of claim 1 wherein the series resistance compensation circuit implements a first algorithm to predict and compensate for a series resistance of a cell; and
the pipette compensation circuit implements a second algorithm to compensate for a capacitance of a pipette.

3. The electronic device of claim 2 wherein the whole-cell compensation circuit implements a third algorithm to compensate for a capacitance of the cell.

4. The electronic device of claim 3 wherein the first circuit is a summing node.

5. The electronic device of claim 4 wherein the first analog circuit is a headstage circuit comprising a first amplifier having a non-inverting input coupled to receive the analog command signal and an inverting input coupled to receive the analog pipette compensation signal via a first capacitor.

6. The electronic device of claim 5 further comprising a first impedance coupled between inverting input and an output of the first amplifier of the headstage circuit.

7. The electronic device of claim 1 wherein the series resistance compensation circuit comprises a first filter and a first gain stage, and the pipette compensation circuit and whole-cell compensation circuit each comprise a second filter and a second gain stage.

8. The electronic device of claim 1 wherein the series resistance compensation circuit implements a first algorithm to predict and compensate for a series resistance of a cell, and the pipette compensation circuit implements a second algorithm to compensate for a capacitance of a pipette and the whole-cell compensation circuit implements a third algorithm to compensate for a capacitance of the cell.

9. An electronic device comprising:
a memory to store information for a digital waveform;
a digital waveform generator to receive the information and use the information to generate the digital waveform, wherein the digital waveform generator is a synchronous digital hardware circuit;
a processing circuit to receive the digital waveform and to generate a digital command signal, wherein the processing circuit comprises a synchronous digital hardware circuit;
a first digital-to-analog converter to convert the digital command signal to an analog command signal;
a first analog circuit to receive the analog command signal and to provide a first analog voltage at a first terminal, wherein the first analog voltage generates a first analog current, the first analog circuit further to provide an analog headstage output based on the first analog current;
a first analog-to-digital converter to receive the analog headstage output and to digitize the analog headstage output to generate a digital headstage output;
the processing circuit to process the digital headstage output and to generate a digital pipette compensation signal; and
a second digital-to-analog converter to convert the digital pipette compensation signal to an analog pipette compensation signal and to provide the analog pipette compensation signal to the first terminal,
wherein the digital waveform generator and the processing circuit are implemented on a field-programmable gate array,
wherein the processing circuit further generates a digital whole-cell compensation signal, and
wherein the electronic device further comprises a third digital-to-analog converter to convert the digital whole-cell compensation signal to an analog whole-cell compensation signal and to provide the analog whole-cell compensation signal to the first terminal.

10. The electronic device of claim 9 wherein the first terminal is configured to provide the first analog voltage to a pipette when the pipette is in contact with a cell.

11. The electronic device of claim 10 wherein the analog pipette compensation signal is provided to the first terminal through a first capacitor and the analog whole-cell compensation signal is provided to the first terminal through a second capacitor.

12. The electronic device of claim 10 wherein the processing circuit comprises:
a series resistance compensation circuit to provide the digital command signal to the first digital-to-analog converter and to implement a first algorithm to predict and compensate for a series resistance of a cell;
a pipette compensation circuit to provide the digital pipette compensation signal to the second digital-to-analog converter and to implement a second algorithm to compensate for a capacitance of a pipette; and
a whole-cell compensation circuit to provide the digital whole-cell compensation signal to the third digital-to-analog converter and to implement a third algorithm to compensate for a capacitance of the cell.

13. The electronic device of claim 9 wherein the field-programmable gate array is controlled by a micro-controller and wherein the micro-controller is controlled by a host computer.

14. The electronic device of claim 9 wherein the processing circuit comprises:
a series resistance compensation circuit to provide the digital command signal to the first digital-to-analog converter and to implement a first algorithm to predict and compensate for a series resistance of a cell; and
a pipette compensation circuit to provide the digital pipette compensation signal to the second digital-to-analog converter and to implement a second algorithm to compensate for a capacitance of a pipette.

15. An electronic device comprising:
a first amplifier having a first input coupled to a first terminal, and a second input;
a first impedance coupled between the first input of the first amplifier and an output of the first amplifier;
a first analog-to-digital converter having an input coupled to the output of the first amplifier;
a processing circuit coupled to the output of the first analog-to-digital converter, the processing circuit comprising:
a memory to store information for a digital waveform;
a digital waveform generator to receive the information and use the information to generate the digital waveform, wherein the digital waveform generator is a synchronous digital hardware circuit;
a series resistance compensation circuit having an input to receive the digital waveform and comprising a first filter and a first gain stage, wherein the series resistance compensation circuit is a synchronous digital hardware circuit;
a pipette compensation circuit having an input to receive an output from the series resistance compensation circuit and comprising a second filter and a second gain stage, wherein the pipette compensation circuit is a synchronous digital hardware circuit;
a whole-cell compensation circuit having an input to receive the digital waveform and comprising a third filter and a third gain stage to generate a whole-cell compensation signal, wherein the whole-cell compensation circuit is a synchronous digital hardware circuit; and
a summing node coupled to an output of the first analog-to-digital converter to receive a digital headstage output signal and coupled to subtract the whole-cell compensation signal from the digital headstage output signal and to provide an output of the summing node to the series resistance compensation circuit;
a first digital-to-analog converter having an input coupled to an output of the series resistance compensation circuit in the processing circuit and an output coupled to the second input of the first amplifier; and
a second digital-to-analog converter having an input coupled to an output of pipette compensation circuit in the processing circuit and an output coupled to the first terminal,
wherein the digital waveform generator, the series resistance compensation circuit, the pipette compensation circuit and the whole-cell compensation circuit are implemented on a field-programmable gate array.

16. The electronic device of claim 15 wherein the first input of the first amplifier is an inverting input and the second input of the first amplifier is a non-inverting input.

17. The electronic device of claim 16 wherein the output of the second digital-to-analog converter is coupled to the first terminal via a first capacitor.

18. The electronic device of claim 15 wherein the series resistance compensation circuit implements a first algorithm to predict and compensate for a series resistance of a cell, the pipette compensation circuit implements a second algorithm to compensate for a capacitance of a pipette and the whole-cell compensation circuit implements a third algorithm to compensate for a capacitance of the cell.

* * * * *